US012788488B2

(12) United States Patent
Schultheis

(10) Patent No.: US 12,788,488 B2
(45) Date of Patent: Nov. 10, 2026

(54) CATHETER INFLATION TUBE FOR USE IN INTRAVASCULAR LITHOTRIPSY

(71) Applicant: Boston Scientific Scimed, Inc., Maple Grove, MN (US)

(72) Inventor: Eric Schultheis, San Clemente, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 366 days.

(21) Appl. No.: 18/137,653

(22) Filed: Apr. 21, 2023

(65) Prior Publication Data

US 2023/0338089 A1 Oct. 26, 2023

Related U.S. Application Data

(60) Provisional application No. 63/334,553, filed on Apr. 25, 2022.

(51) Int. Cl.

*A61M 25/10* (2013.01)
*A61B 18/26* (2006.01)
*A61B 18/00* (2006.01)

(52) U.S. Cl.

CPC ...... *A61B 18/26* (2013.01); *A61B 2018/0022* (2013.01); *A61B 2018/00369* (2013.01);
(Continued)

(58) Field of Classification Search

CPC .............. A61M 25/104; A61M 25/023; A61M 2025/1056; A61M 2025/0183;
(Continued)

(56) References Cited

U.S. PATENT DOCUMENTS

| | | | |
|---|---|---|---|
| 4,649,924 | A | 3/1987 | Taccardi |
| 4,699,147 | A | 10/1987 | Chilson et al. |

(Continued)

FOREIGN PATENT DOCUMENTS

| | | |
|---|---|---|
| AU | 2017205323 | 7/2017 |
| AU | 2022227829 | 9/2022 |

(Continued)

OTHER PUBLICATIONS

Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.

(Continued)

*Primary Examiner* — Katherine H Schwiker
(74) *Attorney, Agent, or Firm* — SEAGER, TUFTE & WICKHEM, LLP

(57) ABSTRACT

A catheter system for treating a treatment site within or adjacent to a vessel wall or a heart valve. In various embodiments, the catheter system includes a balloon and an inflation tube. The balloon has a balloon interior. The inflation tube is configured to guide a flow of an inflation fluid into the balloon interior. The inflation tube has an inflation lumen. The inflation tube is movable between (i) a first configuration wherein the inflation lumen has a first cross-sectional area, and (ii) a second configuration wherein the inflation lumen has a second cross-sectional area that is less than the first cross-sectional area. In various alternative embodiments, the inflation tube can be biased toward the second configuration or the first configuration. The inflation tube can include a tube wall that varies in thickness.

20 Claims, 6 Drawing Sheets

(52) U.S. Cl.
CPC . *A61B 2018/0041* (2013.01); *A61B 2018/263* (2013.01); *A61B 2018/266* (2013.01); *A61M 2025/1061* (2013.01)

(58) Field of Classification Search
CPC .. A61M 2025/0025; A61M 2025/0024; A61B 18/26; A61B 2018/022
See application file for complete search history.

(56) References Cited

U.S. PATENT DOCUMENTS 4,799,479 A 1/1989 Spears
4,850,351 A 7/1989 Herman
4,913,142 A 4/1990 Kittrell et al.
4,932,954 A 6/1990 Wondrazek et al.
4,955,895 A 9/1990 Suglyama
4,960,108 A 10/1990 Reichel et al.
4,994,059 A 2/1991 Kosa et al.
4,998,930 A 3/1991 Lundahl
5,019,075 A 5/1991 Spears et al.
5,034,010 A 7/1991 Kittrell et al.
5,041,121 A 8/1991 Wondrazek et al.
5,057,106 A 10/1991 Kasevich et al.
5,082,343 A 1/1992 Coult et al.
5,093,877 A 3/1992 Aita et al.
5,104,391 A 4/1992 Ingle
5,104,392 A 4/1992 Kittrell et al.
5,109,452 A 4/1992 Selvin et al.
5,116,227 A 5/1992 Levy
5,126,165 A 6/1992 Akihama et al.
5,152,768 A 10/1992 Bhatta
5,173,049 A 12/1992 Levy
5,176,674 A 1/1993 Hofmann
5,181,921 A 1/1993 Makita et al.
5,188,632 A 2/1993 Goldenberg
5,200,838 A 4/1993 Nudelman
5,209,730 A * 5/1993 Sullivan ............ A61M 25/0108 600/585
5,269,777 A 12/1993 Doiron
5,290,277 A 3/1994 Vercimak et al.
5,324,282 A 6/1994 Dodick
5,328,472 A 7/1994 Steinke et al.
5,336,184 A 8/1994 Teirstein
5,363,458 A 11/1994 Pan
5,372,138 A 12/1994 Crowley
5,387,225 A 2/1995 Euteneur
5,400,428 A 3/1995 Grace
5,410,797 A 5/1995 Steinke et al.
5,417,689 A 5/1995 Fine
5,422,926 A 6/1995 Smith
5,431,647 A 7/1995 Purcell
5,454,809 A 10/1995 Janssen
5,456,680 A 10/1995 Taylor
5,466,222 A * 11/1995 Ressemann ........... A61M 29/02 604/524
5,474,537 A 12/1995 Solar
5,496,311 A 3/1996 Abele et al.
5,509,917 A 4/1996 Cecchetti
5,519,798 A 5/1996 Shahid
5,540,679 A 7/1996 Fram
5,562,620 A * 10/1996 Klein .................. A61M 25/104 604/509
5,562,657 A 10/1996 Griffin
5,598,494 A 1/1997 Behrmann et al.
5,609,606 A 3/1997 O'Boyle
5,611,807 A 3/1997 O'Boyle
5,637,877 A 6/1997 Sinofsky
5,661,829 A 8/1997 Zheng
5,697,377 A 12/1997 Wittkamph
5,718,241 A 2/1998 Ben-Haim et al.
5,729,583 A 3/1998 Tang
5,764,843 A 6/1998 Macken et al.
5,772,609 A 6/1998 Nguyen et al.
5,810,776 A * 9/1998 Bacich ............... A61B 17/3421 604/131
5,860,974 A 1/1999 Abele
5,891,135 A 4/1999 Jackson et al.
5,906,611 A 5/1999 Dodick et al.
5,944,697 A 8/1999 Benett et al.
6,007,514 A 12/1999 Nita
6,015,404 A 1/2000 Altshuler
6,080,119 A 6/2000 Schwarze et al.
6,096,013 A * 8/2000 Hakky .................. A61M 25/04 604/349
6,123,923 A 9/2000 Unger
6,139,510 A 10/2000 Palermo
6,186,963 B1 2/2001 Schwarze et al.
6,203,537 B1 3/2001 Adrian
6,210,404 B1 4/2001 Shadduck
6,339,470 B1 1/2002 Papademetriou et al.
6,356,575 B1 3/2002 Fukumoto
6,368,318 B1 4/2002 Visuri et al.
6,423,055 B1 7/2002 Farr
6,500,174 B1 12/2002 Maguire et al.
6,514,203 B2 2/2003 Bukshpan
6,514,249 B1 2/2003 Maguire
6,524,251 B2 2/2003 Rabiner et al.
6,538,739 B1 3/2003 Visuri et al.
6,544,218 B1 4/2003 Choi
6,548,010 B1 4/2003 Stivland et al.
6,560,387 B1 5/2003 Hehlen et al.
6,607,502 B1 8/2003 Maguire et al.
6,631,220 B1 10/2003 Liang et al.
6,652,547 B2 11/2003 Rabiner et al.
6,666,834 B2 12/2003 Restle et al.
6,702,781 B1 3/2004 Reifart et al.
6,773,447 B2 8/2004 Laguna
6,824,554 B1 11/2004 Jang
6,849,994 B1 2/2005 White et al.
6,890,317 B2 5/2005 Gerdts et al.
6,947,785 B1 9/2005 Beatty et al.
6,966,890 B2 11/2005 Coyle et al.
6,978,168 B2 12/2005 Beatty et al.
6,990,370 B1 1/2006 Beatty et al.
7,273,470 B2 9/2007 Wantink
7,309,324 B2 12/2007 Hayes et al.
7,367,967 B2 5/2008 Eidenschink
7,470,240 B2 12/2008 Schultheiss et al.
7,539,231 B1 5/2009 Honea et al.
7,569,032 B2 8/2009 Naimark et al.
7,599,588 B2 10/2009 Eberle et al.
7,641,646 B2 1/2010 Kennedy, II
7,691,079 B2 4/2010 Gobel
7,713,260 B2 5/2010 Lessard
7,758,572 B2 7/2010 Weber et al.
7,762,984 B2 7/2010 Kumoyama et al.
7,810,395 B2 10/2010 Zhou
7,850,685 B2 12/2010 Kunis et al.
7,867,178 B2 1/2011 Simnacher
7,909,797 B2 3/2011 Kennedy, II et al.
7,942,850 B2 5/2011 Levit et al.
7,967,781 B2 6/2011 Simpson et al.
7,972,299 B2 7/2011 Carter
7,985,189 B1 7/2011 Ogden et al.
8,021,328 B2 9/2011 Lee
8,029,473 B2 10/2011 Carter
8,043,256 B2 10/2011 Hansen
8,066,732 B2 11/2011 Paul et al.
8,088,121 B2 1/2012 Nishide
8,157,760 B2 4/2012 Criado et al.
8,162,859 B2 4/2012 Schultheiss et al.
8,166,825 B2 5/2012 Zhou
8,192,368 B2 6/2012 Woodruff
8,197,505 B2 6/2012 Hirszowicz et al.
8,246,643 B2 8/2012 Nita
8,267,886 B2 9/2012 Ewing
8,292,913 B2 10/2012 Warnack
8,328,820 B2 12/2012 Diamant
8,364,235 B2 1/2013 Kordis et al.
8,372,034 B2 2/2013 Levit
8,382,738 B2 2/2013 Simpson et al.
8,414,527 B2 4/2013 Mallaby
8,419,613 B2 4/2013 Saadat
8,439,890 B2 5/2013 Beyar

(56) References Cited

U.S. PATENT DOCUMENTS

| | | | |
|---|---|---|---|
| 8,556,813 | B2 | 10/2013 | Cashman et al. |
| 8,556,851 | B2 | 10/2013 | Hirszowicz |
| 8,574,247 | B2 | 11/2013 | Adams et al. |
| 8,657,814 | B2 | 2/2014 | Werneth |
| 8,709,075 | B2 | 4/2014 | Adams et al. |
| 8,728,091 | B2 | 5/2014 | Hakala et al. |
| 8,734,424 | B2 | 5/2014 | Watanabe |
| 8,747,416 | B2 | 6/2014 | Hakala et al. |
| 8,784,362 | B2 | 7/2014 | Boutilette |
| 8,834,510 | B2 | 9/2014 | Wilson et al. |
| 8,888,788 | B2 | 11/2014 | Hakala et al. |
| 8,956,371 | B2 | 2/2015 | Hawkins et al. |
| 8,956,374 | B2 | 2/2015 | Hawkins et al. |
| 8,986,339 | B2 | 3/2015 | Warnack |
| 8,992,519 | B2 | 3/2015 | Kim et al. |
| 8,992,817 | B2 | 3/2015 | Stamberg |
| 9,005,216 | B2 | 4/2015 | Hakala et al. |
| 9,011,462 | B2 | 4/2015 | Adams et al. |
| 9,011,463 | B2 | 4/2015 | Adams et al. |
| 9,011,511 | B2 | 4/2015 | Gregorich |
| 9,044,575 | B2 | 6/2015 | Beasley et al. |
| 9,044,618 | B2 | 6/2015 | Hawkins et al. |
| 9,044,619 | B2 | 6/2015 | Hawkins et al. |
| 9,056,185 | B2 | 6/2015 | Fischell et al. |
| 9,072,534 | B2 | 7/2015 | Adams et al. |
| 9,089,669 | B2 | 7/2015 | Haslinger et al. |
| 9,131,949 | B2 | 9/2015 | Coleman et al. |
| 9,138,249 | B2 | 9/2015 | Adams et al. |
| 9,138,260 | B2 | 9/2015 | Miller et al. |
| 9,180,280 | B2 | 11/2015 | Hawkins et al. |
| 9,220,521 | B2 | 12/2015 | Hawkins et al. |
| 9,237,984 | B2 | 1/2016 | Hawkins et al. |
| 9,254,169 | B2 | 2/2016 | Long et al. |
| 9,282,984 | B2 | 3/2016 | Nita |
| 9,283,359 | B2 | 3/2016 | Pepper |
| 9,289,132 | B2 | 3/2016 | Ghaffari et al. |
| 9,289,224 | B2 | 3/2016 | Adams et al. |
| 9,289,319 | B2 | 3/2016 | Pacetti et al. |
| 9,320,530 | B2 | 4/2016 | Grace |
| 9,333,000 | B2 | 5/2016 | Hakala et al. |
| 9,339,632 | B2 | 5/2016 | Eidenschink et al. |
| 9,364,645 | B2 | 6/2016 | Erikawa |
| 9,375,223 | B2 | 6/2016 | Wallace |
| 9,421,025 | B2 | 8/2016 | Hawkins et al. |
| 9,433,428 | B2 | 9/2016 | Hakala et al. |
| 9,433,745 | B2 | 9/2016 | Cully |
| 9,504,809 | B2 | 11/2016 | Bo |
| 9,510,887 | B2 | 12/2016 | Burnett |
| 9,522,012 | B2 | 12/2016 | Adams |
| 9,554,815 | B2 | 1/2017 | Adams et al. |
| 9,555,267 | B2 | 1/2017 | Ein-Gal |
| 9,566,209 | B2 | 2/2017 | Katragadda et al. |
| 9,579,114 | B2 | 2/2017 | Mantell et al. |
| 9,579,492 | B2 | 2/2017 | Simpson |
| 9,585,684 | B2 | 3/2017 | Nita et al. |
| 9,592,328 | B2 | 3/2017 | Jeevanandam |
| 9,603,506 | B2 | 3/2017 | Goldfarb et al. |
| 9,629,567 | B2 | 4/2017 | Porath et al. |
| 9,642,673 | B2 | 5/2017 | Adams |
| 9,662,069 | B2 | 5/2017 | De Graff et al. |
| 9,687,166 | B2 | 6/2017 | Subramaniam |
| 9,700,655 | B2 | 7/2017 | Laudenslager et al. |
| 9,730,715 | B2 | 8/2017 | Adams |
| 9,737,361 | B2 | 8/2017 | Magana |
| 9,764,142 | B2 | 9/2017 | Imran |
| 9,782,570 | B2 | 10/2017 | Hirszowicz |
| 9,814,476 | B2 | 11/2017 | Adams et al. |
| 9,833,348 | B2 | 12/2017 | Jordan et al. |
| 9,839,764 | B2 | 12/2017 | Chouinard |
| 9,861,377 | B2 | 1/2018 | Mantell et al. |
| 9,867,629 | B2 | 1/2018 | Hawkins et al. |
| 9,878,135 | B2 | 1/2018 | Holzapfel et al. |
| 9,894,756 | B2 | 2/2018 | Weinkam et al. |
| 9,901,704 | B2 | 2/2018 | Appling |
| 9,955,946 | B2 | 5/2018 | Miller et al. |
| 9,974,963 | B2 | 5/2018 | Imran |
| 9,974,970 | B2 | 5/2018 | Nuta et al. |
| 9,993,292 | B2 | 6/2018 | Adams et al. |
| 10,039,561 | B2 | 8/2018 | Adams et al. |
| 10,076,384 | B2 | 9/2018 | Kasprzyk |
| 10,086,175 | B2 | 10/2018 | Torres et al. |
| 10,124,153 | B2 | 11/2018 | Feig |
| 10,136,829 | B2 | 11/2018 | Deno et al. |
| 10,149,690 | B2 | 12/2018 | Hawkins et al. |
| 10,159,505 | B2 | 12/2018 | Hakala et al. |
| 10,194,994 | B2 | 2/2019 | Deno et al. |
| 10,201,387 | B2 | 2/2019 | Grace et al. |
| 10,206,698 | B2 | 2/2019 | Hakala et al. |
| 10,226,265 | B2 | 3/2019 | Ku et al. |
| 10,245,410 | B2 | 4/2019 | Aggerholm |
| 10,327,846 | B1 | 6/2019 | Stark et al. |
| 10,328,290 | B2 | 6/2019 | Zhou et al. |
| 10,357,264 | B2 | 7/2019 | Kat-Kuoy |
| 10,405,923 | B2 | 9/2019 | Yu et al. |
| 10,406,031 | B2 | 9/2019 | Thyzel |
| 10,406,318 | B2 | 9/2019 | Williams |
| 10,420,569 | B2 | 9/2019 | Adams |
| 10,439,791 | B2 | 10/2019 | Kalhan |
| 10,441,300 | B2 | 10/2019 | Hawkins |
| 10,449,339 | B2 | 10/2019 | Wilson et al. |
| 10,463,430 | B2 | 11/2019 | Dick |
| 10,478,202 | B2 | 11/2019 | Adams et al. |
| 10,517,620 | B2 | 12/2019 | Adams |
| 10,517,621 | B1 | 12/2019 | Hakala et al. |
| 10,537,287 | B2 | 1/2020 | Braido et al. |
| 10,555,744 | B2 | 2/2020 | Nguyen et al. |
| 10,561,428 | B2 | 2/2020 | Eggert et al. |
| 10,583,277 | B2 | 3/2020 | Rundquist |
| 10,589,073 | B2 | 3/2020 | Mallaby |
| 10,617,850 | B2 | 4/2020 | Tal |
| 10,646,240 | B2 | 5/2020 | Betelia et al. |
| 10,668,245 | B2 | 6/2020 | Kanae |
| 10,682,178 | B2 | 6/2020 | Adams et al. |
| 10,695,531 | B2 | 6/2020 | Suzuki |
| 10,702,293 | B2 | 7/2020 | Adams et al. |
| 10,709,462 | B2 | 7/2020 | Nguyen et al. |
| 10,709,872 | B2 | 7/2020 | Alvarez et al. |
| 10,758,255 | B2 | 9/2020 | Adams |
| 10,797,684 | B1 | 10/2020 | Benz et al. |
| 10,799,688 | B2 | 10/2020 | Calhoun |
| 10,842,567 | B2 | 11/2020 | Grace et al. |
| 10,850,075 | B2 | 12/2020 | Tarunaga |
| 10,857,329 | B2 | 12/2020 | Davies |
| 10,933,225 | B2 | 3/2021 | Campbell |
| 10,952,740 | B2 | 3/2021 | Dasnurkar et al. |
| 10,952,790 | B2 | 3/2021 | Haverkost et al. |
| 10,959,743 | B2 | 3/2021 | Adams et al. |
| 10,966,737 | B2 | 4/2021 | Nguyen |
| 10,967,156 | B2 | 4/2021 | Gulachenski |
| 10,973,538 | B2 | 4/2021 | Hakala et al. |
| 10,974,028 | B2 | 4/2021 | Buller et al. |
| 10,980,987 | B2 | 4/2021 | Tarunaga |
| 11,000,299 | B2 | 5/2021 | Hawkins et al. |
| 11,020,135 | B1 | 6/2021 | Hawkins |
| 11,026,707 | B2 | 6/2021 | Ku et al. |
| 11,040,176 | B2 | 6/2021 | Blanchard et al. |
| 11,058,492 | B2 | 7/2021 | Grace et al. |
| 11,076,874 | B2 | 8/2021 | Hakala et al. |
| 11,116,939 | B2 | 9/2021 | Jamous et al. |
| 11,141,131 | B2 | 10/2021 | Stigall |
| 11,179,169 | B2 | 11/2021 | Brouillete et al. |
| 11,207,493 | B2 | 12/2021 | Suzuki et al. |
| 11,213,661 | B2 | 1/2022 | Spindler |
| 11,229,772 | B2 | 1/2022 | Nita |
| 11,229,776 | B2 | 1/2022 | Kugler et al. |
| 11,246,659 | B2 | 2/2022 | Grace et al. |
| 11,253,681 | B2 | 2/2022 | Williams |
| 11,266,817 | B2 | 3/2022 | Cope et al. |
| 11,389,171 | B2 | 7/2022 | Goldsmith |
| 11,389,628 | B2 | 7/2022 | Spencer |
| 11,395,669 | B2 | 7/2022 | O'Malley et al. |
| 11,399,862 | B2 | 8/2022 | Massimini et al. |
| 11,406,452 | B2 | 8/2022 | Efremkin |
| 11,406,799 | B2 | 8/2022 | McEvaddy et al. |

(56) References Cited

U.S. PATENT DOCUMENTS 11,484,327 B2 11/2022 Anderson et al.
11,540,848 B2 1/2023 Cai et al.
11,564,729 B2 1/2023 Walzman
11,602,363 B2 3/2023 Nguyen
11,633,200 B2 4/2023 Anderson et al.
11,672,585 B2 6/2023 Schultheis
11,672,599 B2 6/2023 Schultheis et al.
11,707,323 B2 7/2023 Schultheis et al.
11,771,449 B2 10/2023 Adams et al.
11,779,363 B2 10/2023 Vo
11,826,530 B2 11/2023 Suzuki
11,839,391 B2 12/2023 Schultheis et al.
11,911,054 B2 2/2024 Singla
11,911,056 B2 2/2024 Anderson et al.
11,918,285 B2 3/2024 Sun et al.
11,944,331 B2 4/2024 Anderson et al.
11,950,793 B2 4/2024 Nguyen
12,011,185 B2 6/2024 Vo
12,023,098 B2 7/2024 Nguyen
12,035,932 B1 7/2024 Nunes
12,076,077 B2 9/2024 Mori
12,144,516 B2 11/2024 Betelia
12,178,458 B1 12/2024 Betelia et al.
12,193,691 B2 1/2025 Adams
2001/0016761 A1 8/2001 Rudie
2001/0018569 A1 8/2001 Erbel
2001/0020164 A1 9/2001 Papademetriou
2001/0049464 A1 12/2001 Ganz
2001/0051784 A1 12/2001 Brisken
2002/0045811 A1 4/2002 Kittrell et al.
2002/0052621 A1 5/2002 Fried et al.
2002/0065512 A1 5/2002 Fjield et al.
2002/0082553 A1 6/2002 Duchamp
2002/0183620 A1 12/2002 Tearney
2002/0183729 A1 12/2002 Farr et al.
2002/0188204 A1 12/2002 McNamara et al.
2003/0009157 A1 1/2003 Levine et al.
2003/0050632 A1 3/2003 Fjield et al.
2003/0065316 A1 4/2003 Levine et al.
2003/0114901 A1 6/2003 Loeb et al.
2003/0125719 A1 7/2003 Furnish
2003/0144654 A1 7/2003 Hilal
2003/0176873 A1 9/2003 Chernenko et al.
2004/0002677 A1 1/2004 Gentsler
2004/0024349 A1 2/2004 Flock et al.
2004/0073251 A1 4/2004 Weber
2004/0097996 A1 5/2004 Rabiner
2004/0133254 A1 7/2004 Sterzer et al.
2004/0162508 A1 8/2004 Uebelacker
2004/0210278 A1 10/2004 Boll
2004/0243119 A1 12/2004 Lane et al.
2004/0249401 A1 12/2004 Rabiner
2004/0254570 A1 12/2004 Hadsjicostis
2005/0010095 A1 1/2005 Stewart et al.
2005/0021013 A1 1/2005 Visuri
2005/0080396 A1 4/2005 Rontal
2005/0113722 A1 5/2005 Schultheiss
2005/0171437 A1 8/2005 Carberry
2005/0171527 A1 8/2005 Bhola
2005/0251131 A1 11/2005 Lesh
2005/0259319 A1 11/2005 Brooker
2005/0273014 A1 12/2005 Gianchandani et al.
2005/0277839 A1 12/2005 Alderman et al.
2006/0033241 A1 2/2006 Schewe et al.
2006/0058739 A1* 3/2006 Smith ............... A61M 25/0668
604/246
2006/0084966 A1 4/2006 Maguire et al.
2006/0098921 A1 5/2006 Benaron et al.
2006/0142703 A1 6/2006 Carter
2006/0190022 A1 8/2006 Beyar et al.
2006/0200039 A1 9/2006 Brockway et al.
2006/0221528 A1 10/2006 Li et al.
2006/0241524 A1 10/2006 Lee et al.
2006/0241572 A1 10/2006 Zhou
2006/0241733 A1 10/2006 Zhang et al.
2006/0270976 A1 11/2006 Savage et al.
2007/0027524 A1 2/2007 Johnson
2007/0043340 A1 2/2007 Thyzel
2007/0060990 A1 3/2007 Satake
2007/0088380 A1 4/2007 Hirszowicz et al.
2007/0118057 A1 5/2007 Ein-gal
2007/0142779 A1 6/2007 Duane
2007/0142819 A1 6/2007 El-Nounou et al.
2007/0142821 A1 6/2007 Hennessy et al.
2007/0142856 A1 6/2007 Jang
2007/0179496 A1 8/2007 Swoyer
2007/0239082 A1 10/2007 Schultheiss et al.
2007/0255270 A1 11/2007 Carney
2007/0264353 A1 11/2007 Myntti et al.
2007/0270897 A1 11/2007 Skerven
2007/0280311 A1 12/2007 Hofmann
2007/0299392 A1 12/2007 Beyar et al.
2008/0033519 A1 2/2008 Burwell
2008/0081950 A1 4/2008 Koenig et al.
2008/0086118 A1 4/2008 Lai
2008/0095714 A1 4/2008 Castella et al.
2008/0097251 A1 4/2008 Babaev
2008/0108867 A1 5/2008 Zhou
2008/0114341 A1 5/2008 Thyzel
2008/0132810 A1 6/2008 Scoseria et al.
2008/0175539 A1 7/2008 Brown
2008/0195088 A1 8/2008 Farr et al.
2008/0214891 A1 9/2008 Slenker et al.
2008/0221550 A1 9/2008 Lee
2008/0281157 A1 11/2008 Miyagi et al.
2008/0296152 A1 12/2008 Voss
2008/0319356 A1 12/2008 Cain et al.
2009/0036803 A1 2/2009 Warlick et al.
2009/0043300 A1 2/2009 Reitmajer et al.
2009/0054881 A1 2/2009 Krespi
2009/0097806 A1 4/2009 Viellerobe et al.
2009/0125007 A1 5/2009 Splinter
2009/0131921 A1 5/2009 Kurtz et al.
2009/0192495 A1 7/2009 Ostrovsky et al.
2009/0240242 A1 9/2009 Neuberger
2009/0247945 A1 10/2009 Levit
2009/0281531 A1 11/2009 Rizoiu
2009/0292296 A1 11/2009 Pansky
2009/0296751 A1 12/2009 Kewitsch et al.
2009/0299327 A1 12/2009 Tilson et al.
2009/0306533 A1 12/2009 Rousche
2009/0312768 A1 12/2009 Hawkins et al.
2010/0016862 A1 1/2010 Hawkins et al.
2010/0036238 A1 2/2010 Neidert
2010/0036294 A1 2/2010 Mantell et al.
2010/0063491 A1 3/2010 Verhagen
2010/0094209 A1 4/2010 Drasler et al.
2010/0114020 A1 5/2010 Hawkins et al.
2010/0114065 A1 5/2010 Hawkins et al.
2010/0125268 A1 5/2010 Gustus et al.
2010/0160838 A1 6/2010 Krespi
2010/0160903 A1 6/2010 Krespi
2010/0168572 A1 7/2010 Sliwa
2010/0168836 A1 7/2010 Kassab
2010/0168862 A1 7/2010 Edie et al.
2010/0179632 A1 7/2010 Bruszewski et al.
2010/0191089 A1 7/2010 Stebler et al.
2010/0198114 A1 8/2010 Novak et al.
2010/0199773 A1 8/2010 Zhou
2010/0222786 A1 9/2010 Kassab
2010/0234875 A1 9/2010 Allex et al.
2010/0256535 A1 10/2010 Novak et al.
2010/0265733 A1 10/2010 O'Leary
2010/0286791 A1 11/2010 Goldsmith
2010/0316333 A1 12/2010 Luther
2011/0034832 A1 2/2011 Cioanta et al.
2011/0059415 A1 3/2011 Kasenbacher
2011/0082452 A1 4/2011 Melsky
2011/0082534 A1 4/2011 Wallace
2011/0118634 A1 5/2011 Golan
2011/0144502 A1 6/2011 Zhou et al.
2011/0184244 A1 7/2011 Kagaya et al.
2011/0208185 A1 8/2011 Diamant et al.
2011/0213349 A1 9/2011 Brown

(56) References Cited

U.S. PATENT DOCUMENTS

2011/0245740 A1 10/2011 Novak et al.
2011/0257641 A1 10/2011 Hastings et al.
2011/0263921 A1 10/2011 Vrba et al.
2011/0275990 A1 11/2011 Besser et al.
2011/0306956 A1 12/2011 Islam
2012/0064141 A1 3/2012 Andreacchi et al.
2012/0071715 A1 3/2012 Beyar et al.
2012/0071867 A1 3/2012 Ryan
2012/0071889 A1 3/2012 Mantell et al.
2012/0089132 A1 4/2012 Dick et al.
2012/0095335 A1 4/2012 Sverdlik et al.
2012/0095461 A1 4/2012 Herscher et al.
2012/0116289 A1 5/2012 Hawkins et al.
2012/0116486 A1 5/2012 Naga et al.
2012/0123331 A1 5/2012 Satake
2012/0123399 A1 5/2012 Belikov
2012/0143131 A1 6/2012 Tun
2012/0157892 A1 6/2012 Reitmajer et al.
2012/0203255 A1 8/2012 Hawkins et al.
2012/0221013 A1 8/2012 Hawkins et al.
2012/0232409 A1 9/2012 Stahmann
2012/0296367 A1 11/2012 Grovender et al.
2012/0323211 A1 12/2012 Ogle
2012/0330293 A1 12/2012 Arai
2013/0030431 A1 1/2013 Adams
2013/0030447 A1 1/2013 Adams
2013/0041355 A1 2/2013 Heeren et al.
2013/0046207 A1 2/2013 Capelli
2013/0046293 A1 2/2013 Arai et al.
2013/0053762 A1 2/2013 Rontal et al.
2013/0060234 A1 3/2013 Besser
2013/0110003 A1 5/2013 Surti
2013/0116714 A1 5/2013 Adams et al.
2013/0165764 A1 6/2013 Scheuermann
2013/0190803 A1 7/2013 Angel et al.
2013/0197614 A1 8/2013 Gustus
2013/0218054 A1 8/2013 Sverdlik et al.
2013/0226131 A1 8/2013 Bacino et al.
2013/0253466 A1 9/2013 Campbell
2013/0274726 A1 10/2013 Takayama
2013/0345617 A1 12/2013 Wallace
2014/0005576 A1 1/2014 Adams
2014/0005706 A1 1/2014 Gelfand et al.
2014/0012186 A1 1/2014 Thyzel
2014/0039002 A1 2/2014 Diodone et al.
2014/0039358 A1 2/2014 Zhou et al.
2014/0039513 A1 2/2014 Hakala
2014/0046229 A1 2/2014 Hawkins et al.
2014/0046353 A1 2/2014 Adams
2014/0052146 A1 2/2014 Curtis et al.
2014/0052147 A1 2/2014 Hakala et al.
2014/0058294 A1 2/2014 Gross et al.
2014/0074111 A1 3/2014 Hakala
2014/0128848 A1 5/2014 Appling et al.
2014/0153087 A1 6/2014 Hutchings et al.
2014/0155990 A1 6/2014 Nyuli
2014/0180069 A1 6/2014 Millett
2014/0180126 A1 6/2014 Millett
2014/0180134 A1 6/2014 Hoseit
2014/0188094 A1 7/2014 Islam
2014/0228829 A1 8/2014 Schmitt
2014/0257144 A1 9/2014 Capelli et al.
2014/0257148 A1 9/2014 Jie
2014/0276573 A1 9/2014 Miesel
2014/0288570 A1 9/2014 Adams
2014/0309536 A1 10/2014 Douk et al.
2014/0336626 A1 11/2014 Jiang
2014/0336637 A1 11/2014 Agrawal
2014/0357997 A1 12/2014 Hartmann
2015/0003900 A1 1/2015 Ullrich et al.
2015/0005576 A1 1/2015 Diodone et al.
2015/0039002 A1 2/2015 Hawkins
2015/0057648 A1 2/2015 Swift et al.
2015/0071591 A1 3/2015 Chen
2015/0073430 A1 3/2015 Hakala et al.
2015/0080875 A1 3/2015 Kasprzyk et al.
2015/0100048 A1 4/2015 Hiereth et al.
2015/0105715 A1 4/2015 Pikus et al.
2015/0119870 A1 4/2015 Rudie
2015/0126990 A1 5/2015 Sharma
2015/0141764 A1 5/2015 Harks et al.
2015/0250542 A1 9/2015 Islam
2015/0276689 A1 10/2015 Watanabe et al.
2015/0313732 A1 11/2015 Fulton, III
2015/0320432 A1 11/2015 Adams
2015/0342678 A1 12/2015 Deladurantaye et al.
2015/0342681 A1 12/2015 Lee
2015/0359432 A1 12/2015 Ehrenreich
2015/0359557 A1 12/2015 Shimokawa
2016/0008016 A1 1/2016 Cioanta et al.
2016/0016016 A1 1/2016 Taylor et al.
2016/0018602 A1 1/2016 Govari et al.
2016/0022294 A1 1/2016 Cioanta et al.
2016/0038087 A1 2/2016 Hunter
2016/0095610 A1 4/2016 Lipowski et al.
2016/0135828 A1 5/2016 Hawkins et al.
2016/0135891 A1 5/2016 Feldman
2016/0143522 A1 5/2016 Ransbury
2016/0151639 A1 6/2016 Scharf et al.
2016/0183819 A1 6/2016 Burnett
2016/0183957 A1 6/2016 Hakala et al.
2016/0184020 A1 6/2016 Kowalewski et al.
2016/0184022 A1 6/2016 Grace et al.
2016/0184023 A1 6/2016 Grace et al.
2016/0184526 A1 6/2016 Beyar
2016/0184570 A1 6/2016 Grace et al.
2016/0228187 A1 8/2016 Gross
2016/0234534 A1 8/2016 Kitahara et al.
2016/0262784 A1 9/2016 Grace et al.
2016/0270806 A1 9/2016 Wallace
2016/0302762 A1 10/2016 Stigall et al.
2016/0324564 A1 11/2016 Gerlach et al.
2016/0331389 A1 11/2016 Hakala et al.
2016/0339204 A1 11/2016 Williams
2016/0367274 A1 12/2016 Wallace
2016/0367275 A1 12/2016 Wallace
2017/0049463 A1 2/2017 Popovic et al.
2017/0056035 A1 3/2017 Adams
2017/0086867 A1 3/2017 Adams
2017/0119469 A1 5/2017 Shimizu et al.
2017/0119470 A1 5/2017 Diamant et al.
2017/0135709 A1 5/2017 Nguyen et al.
2017/0151421 A1 6/2017 Asher
2017/0192242 A1 7/2017 Laycock
2017/0209050 A1 7/2017 Fengler et al.
2017/0265942 A1 9/2017 Grace et al.
2017/0303946 A1 10/2017 Ku et al.
2017/0311965 A1 11/2017 Adams
2018/0008348 A1 1/2018 Grace et al.
2018/0042661 A1 2/2018 Long
2018/0042677 A1 2/2018 Yu et al.
2018/0045897 A1 2/2018 Chia
2018/0049877 A1 2/2018 Venkatasubramanian
2018/0085174 A1 3/2018 Radtke et al.
2018/0092763 A1 4/2018 Dagan et al.
2018/0095287 A1 4/2018 Jeng et al.
2018/0098779 A1 4/2018 Betelia et al.
2018/0152568 A1 5/2018 Thumpudi et al.
2018/0169392 A1 6/2018 Franklin
2018/0214677 A1 8/2018 Tarunaga
2018/0238675 A1 8/2018 Wan
2018/0256250 A1 9/2018 Adams et al.
2018/0280005 A1 10/2018 Parmentier
2018/0303501 A1 10/2018 Hawkins
2018/0303503 A1 10/2018 Eggert et al.
2018/0303504 A1 10/2018 Eggert et al.
2018/0304053 A1 10/2018 Eggert et al.
2018/0323571 A1 11/2018 Brown et al.
2018/0333043 A1 11/2018 Teriluc
2018/0360482 A1 12/2018 Nguyen
2019/0029702 A1 1/2019 De Cicco
2019/0029703 A1 1/2019 Wasdyke et al.
2019/0046762 A1* 2/2019 Rogers ................. A61B 5/0215
2019/0069916 A1 3/2019 Hawkins et al.

(56) References Cited

U.S. PATENT DOCUMENTS

2019/0072378 A1 3/2019 Hane et al.
2019/0097380 A1 3/2019 Luft et al.
2019/0099588 A1 4/2019 Ramanath et al.
2019/0104933 A1 4/2019 Stern
2019/0117242 A1 4/2019 Lawinger
2019/0150960 A1 5/2019 Nguyen et al.
2019/0150961 A1 5/2019 Tozzi
2019/0159792 A1 5/2019 Panian
2019/0167349 A1 6/2019 Shamay
2019/0175111 A1 6/2019 Genereux et al.
2019/0175300 A1 6/2019 Hom
2019/0175372 A1 6/2019 Boyden et al.
2019/0175407 A1 6/2019 Bacher
2019/0209368 A1 7/2019 Park et al.
2019/0232066 A1 8/2019 Lim et al.
2019/0247680 A1 8/2019 Mayer
2019/0262594 A1 8/2019 Ogata et al.
2019/0265419 A1 8/2019 Tayebati
2019/0282249 A1 9/2019 Tran et al.
2019/0282250 A1 9/2019 Tran et al.
2019/0285803 A1 9/2019 Van Zuylen
2019/0321100 A1 10/2019 Masotti et al.
2019/0321101 A1 10/2019 Massoti et al.
2019/0328259 A1 10/2019 Deno et al.
2019/0365400 A1 12/2019 Adams et al.
2019/0380589 A1 12/2019 Lloret
2019/0388002 A1 12/2019 Bozsak et al.
2019/0388110 A1 12/2019 Nguyen et al.
2019/0388133 A1 12/2019 Sharma
2019/0388151 A1 12/2019 Bhawalkar
2019/0388654 A1 12/2019 Chou
2020/0000484 A1 1/2020 Hawkins
2020/0008856 A1 1/2020 Harmouche
2020/0022754 A1 1/2020 Cottone
2020/0038087 A1 2/2020 Harmouche
2020/0046429 A1 2/2020 Tschida et al.
2020/0046949 A1 2/2020 Chisena et al.
2020/0054352 A1 2/2020 Brouillette et al.
2020/0060814 A1 2/2020 Murphy
2020/0061931 A1 2/2020 Brown et al.
2020/0069371 A1 3/2020 Brown et al.
2020/0085458 A1 3/2020 Nguyen et al.
2020/0085459 A1 3/2020 Adams
2020/0101269 A1 4/2020 Hayes
2020/0107960 A1 4/2020 Bacher
2020/0108236 A1 4/2020 Salazar et al.
2020/0129195 A1 4/2020 McGowan et al.
2020/0129741 A1 4/2020 Kawwas
2020/0155812 A1 5/2020 Zhang et al.
2020/0197019 A1 6/2020 Harper
2020/0205890 A1 7/2020 Harlev
2020/0246032 A1 8/2020 Betelia et al.
2020/0289202 A1 9/2020 Miyagawa et al.
2020/0297366 A1 9/2020 Nguyen et al.
2020/0337717 A1 10/2020 Walzman
2020/0345380 A1 11/2020 Boyle et al.
2020/0383724 A1 12/2020 Adams et al.
2020/0397230 A1 12/2020 Massimini et al.
2020/0397453 A1 12/2020 McGowan
2020/0398033 A1 12/2020 McGowan et al.
2020/0405333 A1 12/2020 Massimini et al.
2020/0405391 A1 12/2020 Massimini
2020/0406009 A1 12/2020 Massimini et al.
2020/0406010 A1 12/2020 Massimini et al.
2021/0038237 A1 2/2021 Adams
2021/0085347 A1 3/2021 Phan et al.
2021/0085348 A1 3/2021 Nguyen
2021/0085383 A1 3/2021 Vo et al.
2021/0116302 A1 4/2021 Jean-Ruel
2021/0128241 A1 5/2021 Schultheis
2021/0137598 A1 5/2021 Cook et al.
2021/0153939 A1 5/2021 Cook
2021/0177442 A1 6/2021 Girdhar et al.
2021/0177445 A1 6/2021 Nguyen
2021/0186613 A1 6/2021 Cook
2021/0212765 A1 7/2021 Verhagen
2021/0220052 A1 7/2021 Cook
2021/0220053 A1 7/2021 Cook
2021/0244473 A1 8/2021 Cook et al.
2021/0267685 A1 9/2021 Schultheis
2021/0275247 A1 9/2021 Schultheis
2021/0275249 A1 9/2021 Massimini et al.
2021/0282792 A1 9/2021 Adams et al.
2021/0290259 A1 9/2021 Hakala et al.
2021/0290286 A1 9/2021 Cook
2021/0290305 A1 9/2021 Cook
2021/0298603 A1 9/2021 Feldman
2021/0338258 A1 11/2021 Hawkins et al.
2021/0353359 A1 11/2021 Cook
2021/0369348 A1 12/2021 Cook
2021/0378743 A1 12/2021 Massimini et al.
2021/0378744 A1 12/2021 Fanier et al.
2021/0386479 A1 12/2021 Massimini et al.
2022/0000505 A1 1/2022 Hauser
2022/0000506 A1 1/2022 Hauser
2022/0000507 A1 1/2022 Hauser
2022/0000508 A1 1/2022 Schmitt et al.
2022/0000509 A1 1/2022 Laser et al.
2022/0000551 A1 1/2022 Govari et al.
2022/0001138 A1 1/2022 Howell
2022/0008130 A1 1/2022 Massimini et al.
2022/0008693 A1 1/2022 Humbert et al.
2022/0015785 A1 1/2022 Hakala et al.
2022/0021190 A1 1/2022 Pecquois
2022/0022902 A1 1/2022 Spano
2022/0022912 A1 1/2022 Efremkin
2022/0023528 A1 1/2022 Long et al.
2022/0040454 A1 2/2022 Hamm
2022/0054194 A1 2/2022 Bacher et al.
2022/0071704 A1 3/2022 Le
2022/0168594 A1 6/2022 Mayer
2022/0183738 A1 6/2022 Flores et al.
2022/0218402 A1 7/2022 Schultheis
2022/0249165 A1 8/2022 Cook
2022/0249166 A1 8/2022 Cook et al.
2022/0273324 A1 9/2022 Schultheis
2022/0287732 A1 9/2022 Anderson et al.
2022/0313293 A1 10/2022 Singh
2022/0313359 A1 10/2022 Schultheis et al.
2022/0338890 A1 10/2022 Anderson et al.
2022/0354578 A1 11/2022 Cook
2022/0387106 A1 12/2022 Cook
2023/0013920 A1 1/2023 Massimini
2023/0064371 A1 3/2023 Cook et al.
2023/0137107 A1 5/2023 Cook et al.
2023/0157754 A1 5/2023 Bacher et al.
2023/0200906 A1 6/2023 Cook et al.
2023/0226328 A1* 7/2023 Roewer ............ A61M 25/0032
604/164.03
2023/0233256 A1 7/2023 Cook et al.
2023/0240748 A1 8/2023 Cook et al.
2023/0248376 A1 8/2023 Anderson et al.
2023/0255635 A1 8/2023 Schultheis et al.
2023/0255688 A1 8/2023 Schultheis et al.
2023/0255689 A1 8/2023 Schultheis et al.
2023/0310054 A1 10/2023 Schultheis
2023/0310067 A1 10/2023 Schultheis et al.
2023/0310073 A1 10/2023 Adams et al.
2023/0320576 A1 10/2023 Feldman
2023/0338088 A1 10/2023 Massimini et al.
2023/0338089 A1 10/2023 Schultheis
2023/0414234 A1 12/2023 Anderson et al.
2024/0001076 A1 1/2024 Gelsinger
2024/0016508 A1 1/2024 Kocur
2024/0016544 A1 1/2024 Schultheis et al.
2024/0016545 A1 1/2024 Schultheis et al.
2024/0023813 A1 1/2024 Milner
2024/0032995 A1 2/2024 Schultheis et al.
2024/0033002 A1 2/2024 Cook
2024/0041520 A1 2/2024 Schultheis et al.
2024/0050170 A1 2/2024 Fournier
2024/0050696 A1 2/2024 Japuntich
2024/0058060 A1 2/2024 Cook
2024/0065711 A1 2/2024 Hendrickson

(56) References Cited

U.S. PATENT DOCUMENTS

| | | | |
|---|---|---|---|
| 2024/0065712 | A1 | 2/2024 | Schultheis |
| 2024/0099773 | A1 | 3/2024 | Schabert |
| 2024/0122648 | A1 | 4/2024 | Cook |
| 2024/0165658 | A1 | 5/2024 | Fu |
| 2024/0173044 | A1 | 5/2024 | Chen et al. |
| 2024/0173526 | A1 | 5/2024 | Kofidis |
| 2024/0189543 | A1 | 6/2024 | Salinas |
| 2024/0216062 | A1 | 7/2024 | Cook |
| 2024/0260981 | A1 | 8/2024 | Betelia |
| 2024/0260982 | A1 | 8/2024 | Peterson |
| 2024/0277410 | A1 | 8/2024 | Cook |
| 2024/0277974 | A1 | 8/2024 | Oehler |
| 2024/0277980 | A1 | 8/2024 | O'Neill |
| 2024/0285296 | A1 | 8/2024 | Vo |
| 2024/0285922 | A1 | 8/2024 | Chu |
| 2024/0299051 | A1 | 9/2024 | Sidhu et al. |
| 2024/0307119 | A1 | 9/2024 | Nguyen |
| 2024/0325045 | A1 | 10/2024 | Otake |
| 2024/0382258 | A1 | 11/2024 | Schultheis |
| 2025/0025237 | A1 | 1/2025 | Cook |
| 2025/0040947 | A1 | 2/2025 | Schultheis |

FOREIGN PATENT DOCUMENTS

| | | | |
|---|---|---|---|
| CA | 2229806 | | 3/1997 |
| CA | 2281519 | | 8/1998 |
| CA | 2983655 | | 10/2016 |
| CA | 3209797 | | 9/2022 |
| CN | 102057422 | | 5/2011 |
| CN | 109223100 | | 1/2019 |
| CN | 110638501 | | 1/2020 |
| CN | 110638501 | A | 1/2020 |
| CN | 106794043 | | 3/2020 |
| CN | 107411805 | | 1/2022 |
| CN | 107899126 | | 1/2022 |
| CN | 109475378 | | 1/2022 |
| CN | 113876388 | | 1/2022 |
| CN | 113877044 | | 1/2022 |
| CN | 113907838 | | 1/2022 |
| CN | 113951972 | A | 1/2022 |
| CN | 113951973 | A | 1/2022 |
| CN | 113974765 | | 1/2022 |
| CN | 113974826 | A | 1/2022 |
| CN | 113993463 | | 1/2022 |
| CN | 215384399 | | 1/2022 |
| CN | 215386905 | | 1/2022 |
| CN | 215458400 | | 1/2022 |
| CN | 215458401 | | 1/2022 |
| CN | 215505065 | | 1/2022 |
| CN | 215534803 | | 1/2022 |
| CN | 215537694 | | 1/2022 |
| CN | 215584286 | | 1/2022 |
| CN | 215606068 | | 1/2022 |
| CN | 215651393 | | 1/2022 |
| CN | 215651394 | | 1/2022 |
| CN | 215651484 | | 1/2022 |
| CN | 215653328 | | 1/2022 |
| CN | 114053552 | | 2/2022 |
| CN | 115175625 | | 10/2022 |
| CN | 117752412 | | 3/2024 |
| CN | 118055734 | | 5/2024 |
| DE | 3038445 | A1 | 5/1982 |
| DE | 3836337 | A1 | 4/1990 |
| DE | 3913027 | A1 | 10/1990 |
| DE | 69431758 | | 1/2003 |
| DE | 10230626 | | 1/2004 |
| DE | 202008016760 | | 3/2009 |
| DE | 102007046902 | | 4/2009 |
| DE | 102008034702 | | 1/2010 |
| DE | 102009007129 | | 8/2010 |
| DE | 202010009899 | | 11/2010 |
| DE | 102013201928 | | 8/2014 |
| DE | 102020117713 | | 1/2022 |
| EP | 0119296 | | 9/1984 |
| EP | 0261831 | B1 | 6/1992 |
| EP | 558297 | A2 | 9/1993 |
| EP | 0571306 | A1 | 11/1993 |
| EP | 0547146 | | 7/1995 |
| EP | 1179993 | A1 | 2/2002 |
| EP | 1946712 | | 7/2008 |
| EP | 1946712 | A1 | 7/2008 |
| EP | 1453566 | | 9/2008 |
| EP | 2157569 | | 2/2010 |
| EP | 2470248 | | 7/2012 |
| EP | 2879595 | | 6/2015 |
| EP | 2879595 | A1 | 6/2015 |
| EP | 2944264 | A1 | 6/2015 |
| EP | 3226795 | A1 | 10/2017 |
| EP | 3266487 | | 1/2018 |
| EP | 3318204 | | 5/2018 |
| EP | 2879607 | | 2/2019 |
| EP | 3461438 | A1 | 4/2019 |
| EP | 3473195 | A1 | 4/2019 |
| EP | 2961463 | | 5/2019 |
| EP | 3240603 | | 5/2019 |
| EP | 3197381 | | 3/2020 |
| EP | 3643260 | A1 | 4/2020 |
| EP | 3240494 | | 3/2021 |
| EP | 3522812 | | 12/2021 |
| EP | 3076881 | B1 | 1/2022 |
| EP | 3932342 | | 1/2022 |
| EP | 3936140 | | 1/2022 |
| EP | 3960099 | | 3/2022 |
| EP | 4051154 | | 9/2022 |
| EP | 4129213 | | 2/2023 |
| EP | 4277537 | | 11/2023 |
| EP | 4297669 | | 1/2024 |
| EP | 4146322 | | 4/2024 |
| EP | 3182931 | | 6/2024 |
| EP | 3950036 | | 8/2024 |
| EP | 4034005 | | 12/2024 |
| GB | 1082397 | | 9/1967 |
| JP | S62275446 | A | 11/1987 |
| JP | H05264763 | | 10/1993 |
| JP | 1996089511 | | 4/1996 |
| JP | H09117407 | | 5/1997 |
| JP | 2001520070 | | 10/2001 |
| JP | 2004519296 | | 7/2004 |
| JP | 2008506447 | | 3/2008 |
| JP | 2008083273 | | 4/2008 |
| JP | 2009519777 | | 5/2009 |
| JP | 2009213589 | | 9/2009 |
| JP | 2011524203 | | 9/2011 |
| JP | 4805208 | | 11/2011 |
| JP | 4808620 | | 11/2011 |
| JP | 2012505050 | | 3/2012 |
| JP | 2014123147 | | 7/2014 |
| JP | A2014516614 | | 7/2014 |
| JP | A2015522344 | | 8/2015 |
| JP | 2015217215 | | 12/2015 |
| JP | 2018538077 | | 12/2018 |
| JP | 2024511710 | | 3/2024 |
| KR | 20050098932 | | 10/2005 |
| KR | 20080040111 | | 5/2008 |
| KR | 20160090877 | A | 8/2016 |
| KR | 20180054041 | | 5/2018 |
| WO | WO9007904 | A1 | 7/1990 |
| WO | WO9105332 | A1 | 4/1991 |
| WO | 9203095 | A1 | 3/1992 |
| WO | WO9208515 | | 5/1992 |
| WO | WO9524867 | | 9/1995 |
| WO | 1999002095 | A1 | 1/1999 |
| WO | 1999020189 | A1 | 4/1999 |
| WO | WO200067648 | | 11/2000 |
| WO | WO2000067648 | A1 | 11/2000 |
| WO | WO0103599 | | 1/2001 |
| WO | WO0103599 | A2 | 1/2001 |
| WO | 20060006169 | A2 | 1/2006 |
| WO | WO2006006169 | | 1/2006 |
| WO | WO2009121017 | | 10/2009 |
| WO | WO2009149321 | A1 | 12/2009 |
| WO | WO2009152352 | | 12/2009 |
| WO | 2010042653 | A1 | 4/2010 |
| WO | WO2011094379 | | 8/2011 |

(56) References Cited

FOREIGN PATENT DOCUMENTS

| | | | |
|---|---|---|---|
| WO | 20110126580 A2 | 10/2011 |
| WO | WO2011126580 | 10/2011 |
| WO | WO2012025833 | 3/2012 |
| WO | WO2012042619 | 4/2012 |
| WO | WO20120052924 A1 | 4/2012 |
| WO | WO2012058156 | 5/2012 |
| WO | WO20120120495 A2 | 9/2012 |
| WO | WO2013119662 | 8/2013 |
| WO | 20130169807 A1 | 11/2013 |
| WO | WO2013169807 | 11/2013 |
| WO | WO2014025397 A1 | 2/2014 |
| WO | WO20140022867 A1 | 2/2014 |
| WO | WO2014138582 | 9/2014 |
| WO | WO2015056662 | 4/2015 |
| WO | WO2015097251 A2 | 7/2015 |
| WO | 20150177790 A1 | 11/2015 |
| WO | WO2016014999 | 1/2016 |
| WO | WO2016089683 A1 | 6/2016 |
| WO | WO2016090175 | 6/2016 |
| WO | WO2016098670 | 6/2016 |
| WO | WO2016109739 | 7/2016 |
| WO | WO2016143556 | 9/2016 |
| WO | WO2016151595 A1 | 9/2016 |
| WO | WO20170192869 A1 | 11/2017 |
| WO | 20180022641 A1 | 2/2018 |
| WO | WO2018022593 A1 | 2/2018 |
| WO | WO2018083666 | 5/2018 |
| WO | 20180175322 A1 | 9/2018 |
| WO | WO2018175322 | 9/2018 |
| WO | WO2018191013 | 10/2018 |
| WO | WO2019200201 A1 | 10/2019 |
| WO | WO2019222843 | 11/2019 |
| WO | WO2020056031 | 3/2020 |
| WO | WO20200086361 A1 | 4/2020 |
| WO | WO2020089876 A1 | 5/2020 |
| WO | WO2020157648 | 8/2020 |
| WO | WO2020256693 | 12/2020 |
| WO | WO2020256898 | 12/2020 |
| WO | WO2020256898 A1 | 12/2020 |
| WO | WO2020256949 | 12/2020 |
| WO | WO2020256949 A1 | 12/2020 |
| WO | WO2020263469 A1 | 12/2020 |
| WO | WO2020263685 A1 | 12/2020 |
| WO | WO2020263687 A1 | 12/2020 |
| WO | WO2020263688 A1 | 12/2020 |
| WO | WO2020263689 A1 | 12/2020 |
| WO | WO2021061451 | 4/2021 |
| WO | WO2021067563 | 4/2021 |
| WO | WO2021086571 A1 | 5/2021 |
| WO | WO2021096922 A1 | 5/2021 |
| WO | WO2021101766 | 5/2021 |
| WO | WO2021101766 A1 | 5/2021 |
| WO | WO2021126762 A1 | 6/2021 |
| WO | WO2021150502 A1 | 7/2021 |
| WO | WO2021162855 A1 | 8/2021 |
| WO | WO2021173417 A1 | 9/2021 |
| WO | WO2021183367 A1 | 9/2021 |
| WO | WO2021183401 A1 | 9/2021 |
| WO | WO2021188233 A1 | 9/2021 |
| WO | WO2021231178 A1 | 11/2021 |
| WO | WO2021247685 A1 | 12/2021 |
| WO | WO2021257425 A1 | 12/2021 |
| WO | WO2022007490 | 1/2022 |
| WO | WO2022008440 | 1/2022 |
| WO | WO2022010767 A1 | 1/2022 |
| WO | WO2022055784 | 3/2022 |
| WO | WO2022125525 | 6/2022 |
| WO | WO2022154954 | 7/2022 |
| WO | WO2022173719 | 8/2022 |
| WO | WO2022183075 | 9/2022 |
| WO | WO2022187058 | 9/2022 |
| WO | WO2022216488 | 10/2022 |
| WO | WO2022240674 | 11/2022 |
| WO | WO2022260932 | 12/2022 |
| WO | WO2023107334 | 6/2023 |
| WO | WO2024079108 | 4/2024 |
| WO | WO2024107418 | 5/2024 |

OTHER PUBLICATIONS

Jones, H. M., et al. "Pulsed dielectric breakdown of pressurized water and salt solutions", Journal of Applied Physics, Jun. 1998, pp. 795-805, vol. 77, No. 2, American Institute of Physics.

Kozulin, I., et al. "The dynamic of the water explosive vaporization on the flat microheater", Journal of Physics: Conference Series, 2018, pp. 1-4, IOP Publishing, Russia.

Cross, F., "Laser Angioplasty", Vascular Medicine Review, 1992, pp. 21-30, Edward Arnold.

Doukas, A. G., et al. "Laser-generated stress waves and their effects on the cell membrane", IEEE Journal of Selected Topics in Quantum Electronics, 1999, pp. 997-1003, vol. 5, Issue 4, IEEE.

Noack, J., et al. "Laser-Induced Plasma Formation in Water at Nanosecond to Femtosecond Time Scales: Calculation of Thresholds, Absorption Coefficients, and Energy Density", IEEE Journal of Quantum Electronics, 1999, pp. 1156-1167, vol. 35, No. 8, IEEE.

Pratsos, A., "The use of Laser for the treatment of coronary artery disease", Bryn Mawr Hospital, 2010.

Li, Xian-Dong, et al. "Influence of deposited energy on shock wave induced by underwater pulsed current discharge", Physics of Plasmas, 2016, vol. 23, American Institute of Physics.

Logunov, S., et al. "Light diffusing optical fiber illumination", Renewable Energy and the Environment Congress, 2013, Corning, NY, USA.

Maxwell, A. D., et al. "Cavitation clouds created by shock scattering from bubbles during histotripsy", Acoustical Society of America, 2011, pp. 1888-1898, vol. 130, No. 4, Acoustical Society of America.

Mcateer, James A., et al. "Ultracal-30 Gypsum Artificial Stones for Research on the Mechinisms of Stone Breakage in Shock Wave Lithotripsy", 2005, pp. 429-434, Springer-Verlag.

Vogel, A., et al. "Mechanisms of Intraocular Photodisruption With Picosecond and Nanosecond Laser Pulses", Lasers in Surgery and Medicine, 1994, pp. 32-43, vol. 15, Wiley-Liss Inc., Lubeck, Germany.

Vogel, A., et al. "Mechanisms of Pulsed Laser Ablation of Biological Tissues", Chemical Reviews, 2003, pp. 577-644, vol. 103, No. 2, American Chemical Society.

Medlight, "Cylindrical light diffuser Model RD-ML", Medlight S.A., Switzerland. 2015.

Medlight, "Cylindircal light diffuser Model RD", Medlight S.A., Switzerland. 2015.

Mayo, Michael E., "Interaction of Laser Radiation with Urinary Calculi", Cranfield University Defense and Security, PhD Thesis, 2009, Cranfield University.

Vogel, A., et al. "Minimization of Cavitation Effects in Pulsed Laser Ablation Illustrated on Laser Angioplasty", Applied Physics, 1996, pp. 173-182, vol. 62, Springer-Verlag.

Mirshekari, G., et al. "Microscale Shock Tube", Journal of Microelectromechanical Systems, 2012, pp. 739-747, vol. 21, No. 3, IEEE.

"Polymicro Sculpted Silica Fiber Tips", Molex, 2013, Molex.

Zhou, J., et al. "Optical Fiber Tips and Their Applications", Polymicro Technologies A Subsidiary of Molex, Nov. 2007.

Liang, Xiao-Xuan, et al. "Multi-Rate-Equation modeling of the energy spectrum of laser-induced conduction band electrons in water", Optics Express, 2019, vol. 27, No. 4, Optical Society of America.

Nachabe, R., et al. "Diagnosis of breast cancer using diffuse optical spectroscopy from 500 to 1600 nm: comparison of classification methods", Journal of Biomedical Optics, 2011, vol. 16(8), SPIE.

Naugol'nykh, K. A., et al. "Spark Discharges in Water", Academy of Sciences USSR Institute of Acoustics, 1971, Nauka Publishing Co., Moscow, USSR.

Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.

(56) References Cited

OTHER PUBLICATIONS

Nyame, Yaw A., et al. "Kidney Stone Models for In Vitro Lithotripsy Research: A Comprehensive Review", Journal of Endourology, Oct. 2015, pp. 1106-1109, vol. 29, No. 10, Mary Ann Liebert Inc., Cleveland, USA.
Ohl, Siew-Wan, et al. "Bubbles with shock waves and ultrasound: a review", Interface Focus, pp. 1-15, vol. 5, The Royal Society Publishing. Oct. 2015.
Zheng, W., "Optical Lenses Manufactured on Fiber Ends", IEEE, 2015, Splicer Engineering, Duncan SC USA.
Dwyer, P. J., et al. "Optically integrating balloon device for photodynamic therapy", Lasers in Surgery and Medicine, 2000, pp. 58-66, vol. 26, Issue 1, Wiley-Liss Inc., Boston MA USA.
"The New Optiguide DCYL700 Fiber Optic Diffuser Series", Optiguide Fiber Optic Spec Sheet, Pinnacle Biologics, 2014, Pinnacle Biologics, Illinois, USA.
Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.
Oshita, D., et al. "Characteristic of Cavitation Bubbles and Shock Waves Generated by Pulsed Electric Discharges with Different Voltages", IEEE, 2012, pp. 102-105, Kumamoto, Japan.
Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.
Murray, A., et al. "Peripheral laser angioplasty with pulsed dye laser and ball tipped optical fibres", The Lancet, 1989, pp. 1471-1474, vol. 2, Issue 8678-8679.
Mohammadzadeh, M., et al. "Photoacoustic Shock Wave Emission and Cavitation from Structured Optical Fiber Tips", Applied Physics Letters, 2016, vol. 108, American Institute of Physics Publishing LLC.
Doukas, A. G., et al. "Physical characteristics and biological effects of laser-induced stress waves", Ultrasound in Medicine and Biology, 1996, pp. 151-164, vol. 22, Issue 2, World Federation for Ultrasound in Medicine and Biology, USA.
Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.
Piedrahita, Francisco S., "Experimental Research Work on a Sub-Millimeter Spark-Gap for Sub Nanosecond Gas Breakdown", Thesis for Universidad Nacional De Colombia, 2012, Bogota, Colombia.
Vogel, A., et al. "Plasma Formation in Water by Picosecond and Nanosecond Nd: YAG Laser Pulses—Part I: Optical Breakdown at Threshold and Superthreshold Irradiance", IEEE Journal of Selected Topics in Quantum Electronics, 1996, pp. 847-859, vol. 2, No. 4, IEEE.
Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.
Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.
Lee, Seung H., et al. "Radial-firing optical fiber tip containing conical-shaped air-pocket for biomedical applications", Optics Express, 2015, vol. 23, No. 16, Optical Society of America.
Hui, C., et al. "Research on sound fields generated by laser-induced liquid breakdown", Optica Applicata, 2010, pp. 898-907, vol. XL, No. 4, Xi'an, China.
Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.
Roberts, Randy M., et al. "The Energy Partition of Underwater Sparks", The Journal of the Acoustical Society of America, 1996, pp. 3465-3475, vol. 99, No. 6, Acoustical Society of America.
Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.
Scepanovic, Obrad R., et al. "Multimodal spectroscopy detects features of vulnerable atherosclerotic plaque", Journal of Biomedical Optics, 2011, pp. 1-10, vol. 16, No. 1, SPIE.
Serruys, P. W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.
Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.
Vogel, A., et al. "Shock-Wave Energy and Acoustic Energy Dissipation After Laser-induced Breakdown", SPIE, 1998, pp. 180-189, vol. 3254, SPIE.
International Search Report and Written Opinion, issued by the EP/ISA, in PCT/US2021/048819, dated Jan. 14, 2022.
"Custom Medical Skived Tubing", Duke Extrusion, 2025. https://www.dukeextrusion.com/tubing-options/skived-tubing.
Davletshin, Yevgeniy R., "A Computational Analysis of Nanoparticle-Mediated Optical Breakdown", A dissertation presented to Ryerson University in Partial Fulfillment of the requirements for the degree of Doctor of Philosophy in the Program of Physics, Toronto, Ontario, CA 2017.
Vogel, A., et al. "Acoustic transient generation by laser-produced cavitation bubbles near solid boundaries", Journal Acoustical Society of America, 1988, pp. 719-731, vol. 84.
Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.
Zheng, W., "Optic Lenses Manufactured on Fiber Ends", 2015, Splicer Engineering AFL, Duncan, SC USA.
Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.
Ali, Ziad A., et al. "Intravascular lithotripsy for treatment of stent underexpansion secondary to severe coronary calcification" 2018, European Society of Cardiology.
Ashok, Praveen C., et al. "Raman spectroscopy bio-sensor for tissue discrimination in surgical robotics—full article", Journal of Biophotonics, 2014, pp. 103-109, vol. 7, No. 1-2.
Ashok, Praveen C., et al. "Raman spectroscopy bio-sensor for tissue discrimination in surgical robotics—proof" Journal of Biophotonics 7, 2014, No. 1-2.
Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.
Bian, D. C., et al. "Study on Breakdown Delay Characteristics Based on High-voltage Pulse Discharge in Water with Hydrostatic Pressure", Journal of Power Technologies 97(2), 2017, pp. 89-102.
Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.
Brodmann, Marianne et al. "Safety and Performance of Lithoplasty for Treatment of Calcified Peripheral Artery Lesions", JACC, 2017, vol. 70, No. 7.
Brouillette, M., "Shock Waves at Microscales", 2003, pp. 3-12, Springer-Verlag.
Mirshekari, G., et al. "Shock Waves in Microchannels", 2013, pp. 259-283, vol. 724, Cambridge University Press.
"Bubble Dynamics and Shock Waves", Springer, 2013, Springer-Verlag, Berlin Heildelberg.

(56) References Cited

OTHER PUBLICATIONS

Hardy, Luke A., et al. "Cavitation Bubble Dynamics During Thulium Fiber Laser Lithotripsy", SPIE, Feb. 29, 2016, vol. 9689, San Francisco, California, USA.
Claverie, A., et al. "Experimental characterization of plasma formation and shockwave propagation induced by high power pulsed underwater electrical discharge", Review of Scientific Instruments, 2014, American Institute of Physics.
Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.
Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.
Cook, Jason R., et al. "Tissue mimicking phantoms for photoacoustic and ultrasonic imaging", Biomedical Optics Express, 2011, vol. 2, No. 11, Optical Society of America.
Deckelbaum, Lawrence I., "Coronary Laser Angioplasty", Lasers in Surgery and Medicine, 1994, pp. 101-110, Wiley-Liss Inc.
Costanzo, F., "Underwater Explosion Phenomena and Shock Physics", Research Gate, 2011.
Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.
De Silva, K., et al. "A Calcific, Undilatable Stenosis Lithoplasty, a New Tool in the Box?", JACC: Cardiovascular Interventions, 2017, vol. 10, No. 3, Elsevier.
Vesselov, L., et al. "Design and performance of thin cylindrical diffusers created in Ge-doped multimode optical fibers", Applied Optics, 2005, pp. 2754-2758, vol. 44, Issue 14, Optical Society of America.
Hutchens, Thomas C., et al. "Detachable fiber optic tips for use in thulium fiber laser lithotripsy", Journal of Biomedical Optics, Mar. 2013, vol. 18(3), SPIE.
Kostanski, Kris L., et al. "Development of Novel Tunable Light Scattering Coating Materials for Fiber Optic Diffusers in Photodynamic Cancer Therapy", Journal of Applied Polymer Science, 2009, pp. 1516-1523, vol. 112, Wiley InterScience.
Kristiansen, M., et al. "High Voltage Water Breakdown Studies", DoD, 1998, Alexandria, VA, USA.
Dwyer, J. R., et al. "A study of X-ray emission from laboratory sparks in air at atmospheric pressure", Journal of Geophysical Research, 2008, vol. 113, American Geophysical Union.
Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.
Shangguan, HanQun et al. "Effects of Material Properties on Laser-induced Bubble Formation in Absorbing Liquids and on Submerged Targets", SPIE, 1997, pp. 783-791, vol. 2869.
Varghese, B., et al. "Effects of polarization and absorption on laser induced optical breakdown threshold for skin rejuvenation", SPIE, Mar. 9, 2016, vol. 9740, SPIE, San Francisco, USA.
Varghese, B., et al. "Effects of polarization and apodization on laser induced optical breakdown threshold", Optics Express, Jul. 29, 2013, vol. 21, No. 15, Optical Society of America.
Bonito, Valentina, "Effects of polarization, plasma and thermal initiation pathway on irradiance threshold of laser induced optical breakdown", Philips Research, 2013, The Netherlands.
Vogel, A. et al. "Energy balance of optical breakdown in water at nanosecond to femtosecond time scales", Applied Physics B 68, 1999, pp. 271-280, Springer-Verlag.
Kang, Hyun W., et al. "Enhanced photocoagulation with catheter based diffusing optical device", Journal of Biomedical Optics, Nov. 2012, vol. 17(11), SPIE.
Esch, E., et al. "A Simple Method for Fabricating Artificial Kidney Stones of Different Physical Properties", National Institute of Health Public Access Author Manuscript, Aug. 2010.
Isner, Jeffrey M., et al. "Excimer Laser Atherectomy", Circulation, Jun. 1990, vol. 81, No. 6, American Heart Association, Dallas, TX, USA.
Israel, Douglas H., et al. "Excimer Laser-Facilitated Balloon Angioplasty of a Nondilateable Lesion", JACC, Oct. 1991, vol. 18, No. 4, American College of Cardiology, New York, USA.
Van Leeuwen, Ton G., et al. "Excimer Laser Induced Bubble: Dimensions, Theory, and Implications for Laser Angioplasty", Lasers in Surgery and Medicine 18, 1996, pp. 381-390, Wiley-Liss Inc., Utrecht, The Netherlands.
Nguyen, H., et al. "Fabrication of multipoint side-firing optical fiber by laser micro-ablation", Optics Letters, May 1, 2017, vol. 42, No. 9, Optical Society of America.
Zheng, W., "Optic Lenses Manufactured on Fiber Ends", 2015, IEEE, Duncan, SC, USA.
Whitesides, George M., et al. "Fluidic Optics", 2006, vol. 6329, SPIE, Cambridge, MA, USA.
Forero, M., et al. "Coronary lithoplasty: a novel treatment for stent underexpansion", Cardiovascular Flashlight, 2018, European Society of Cardiology.
Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.
Roberts, Randy M., et al. "The Energy Partition of Underwater Sparks", The Journal of the Acoustical Society of America, Jun. 1996, pp. 3465-3474, Acoustical Society of America, Austin, TX, USA.
Blackmon, Richard L., et al. "Holmium: YAG Versus Thulium Fiber Laser Lithotripsy", Lasers in Surgery and Medicine, 2010, pp. 232-236, Wiley-Liss Inc.
Varghese, B., "Influence of absorption induced thermal initiation pathway on irradiance threshold for laser induced breakdown", Biomedical Optics Express, 2015, vol. 6, No. 4, Optical Society of America.
Noack, J., "Influence of pulse duration on mechanical effects after laser-induced breakdown in water", Journal of Applied Physics, 1998, pp. 7488-EOA, vol. 83, American Institute of Physics.
Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.
Shen, Yajie et al. "High-peak-power and narrow-linewidth Q-switched Ho: YAG laser in-band pumped at 1931 nm." Applied Physics Express 13.5 (2020): 052006. (Year 2020).
Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.
Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.
Tagawa, Y., et al. "Structure of laser-induced shock wave in water", Japan Society for the Promotion of Science, 2016.
Shen, Y., et al. "Theoretical and experimental studies of directivity of sound field generated by pulsed laser induced breakdown in liquid water", SPIE, 2013, pp. 8796141-8796148, vol. 8796, SPIE.
Preisack, M., et al. "Ultrafast imaging of tissue ablation by a XeCl excimer laser in saline", Lasers in Surgery and Medicine, 1992, pp. 520-527, vol. 12, Wiley-Liss Inc.
Versluis, M., et al. "How Snapping Shrimp Snap: Through Cavitating Bubbles", Science Mag, 2000, pp. 2114-2117, vol. 289, American Association for the Advancement of Science, Washington DC, USA.
Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.
Zhang, Q., et al. "Improved Instruments and Methods for the Photographic Study of Spark-Induced Cavitation Bubbles", Water, 2018, pp. 1-12, vol. 10, No. 1683.

(56) References Cited

OTHER PUBLICATIONS

"Damage threshold of fiber facets", NKT Photonics, 2012, pp. 1-4, Denmark.
Smith, A., et al. "Bulk and surface laser damage of silica by picosecond and nanosecond pulses at 1064 nm", Applied Optics, 2008, pp. 4812-4832, vol. 47, No. 26, Optical Society of America.
Smith, A., et al. "Deterministic Nanosecond Laser-Induced Breakdown Thresholds in Pure and Yb3 Doped Fused Silica", SPIE, 2007, pp. 6453171-64531712, vol. 6453, SPIE.
Sun, X., et al. "Laser Induced Damage to Large Core Optical Fiber by High Peak Power Laser", Specialty Photonics Division, 2010.
Smith, A., et al. "Nanosecond laser-induced breakdown in pure and Yb3 doped fused silica", SPIE, 2007, vol. 6403, SPIE.
Smith, A., et al. "Optical Damage Limits to Pulse Energy From Fibers", IEEE Journal of Selected Topics in Quantum Electronics, 2009, pp. 153-158, vol. 15, No. 1, IEEE.
Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.
Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.
Reichel, E., et al. "Laser-induced Shock Wave Lithotripsy with a Regenerative Energy Converter", Lasers in Medical Science, 1992, pp. 423-425, vol. 7, Bailliere Tindall.
Hardy, L., et al. "Cavitation Bubble Dynamics during Thulium Fiber Laser Lithotripsy", SPIE BiOS, 2016, vol. 9689, SPIE.
Deckelbaum, L., "Coronary Laser Angioplasty", Lasers in Surgery and Medicine, 1994, pp. 101-110, vol. 14, Wiley-Liss Inc., Conneticuit, USA.
Shangguan, H., et al. "Effects of Material Properties on Laser-induced Bubble Formation in Absorbing Liquids and on Submerged Targets", Diagnostic and Therapeutic Cardiovascular Interventions VII, SPIE, 1997, pp. 783-791, vol. 2869, SPIE.
Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.
Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.
Varghese, B., et al. "Influence of absorption induced thermal initiation pathway on irradiance threshold for laser induced breakdown", Biomedical Optics Express, 2015, vol. 6, No. 4, Optical Society of America.
Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.
International Search Report and Written Opinion dated Jun. 27, 2018, in PCT Application Serial No. PCT/US2018/027121.
International Search Report and Written Opinion dated Jul. 20, 2018, in PCT Application Serial No. PCT/US2018/027801.
International Search Report and Written Opinion dated Jul. 20, 2018, in PCT Application Serial No. PCT/US2018/027784.
European Search Report, for European Patent Application No. 18/185,152, mailed Dec. 13, 2018.
International Search Report and Written Opinion dated May 22, 2019, in PCT Application Serial No. PCT/US2019/022009.
International Search Report and Written Opinion dated May 29, 2019, in PCT Application Serial No. PCT/US2019/022016.
International Search Report and Written Opinion dated Jun. 22, 2018, in Application Serial No. NL2019807, issued by the European Patent Office.
Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26, Wiley-Liss Inc.
Chen, Sung-Liang, "Review of Laser-Generated Ultrasound Transmitters and their Applications to All-Optical Ultrasound Transducers and Imaging", Appl. Sci. 2017, 7, 25.
Colchester, R., et al. "Laser-Generated ultrasound with optica fibres using functionalised carbon nanotube composite coatings", Appl. Phys. Lett., 2014, vol. 104, 173504, American Institute of Physics.
Poduval, R., et al. "Optical fiber ultrasound transmitter with electrospun carbon nanotube-polymer composite", Appl. Phys. Lett., 2017, vol. 110, 223701, American Institute of Physics.
Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.
Kim, J., et al. "Optical Fiber Laser-Generated-Focused-Ultrasound Transducers for Intravascular Therapies", IEEE, 2017.
Kang, H., et al. "Enhanced photocoagulation with catheter-based diffusing optical device", Journal of Biomedical Optics, 2012, vol. 17, Issue 11, 118001, SPIE.
International Search Report and Written Opinion dated Jan. 3, 2020, in PCT Application Serial No. PCT/US2019/056579.
Communication Pursuant to Article 94(3) EPC, for European Patent Application No. 18185152.8, mailed Jan. 16, 2019.
European Search Report, for European Patent Application No. 18185152.8, mailed Dec. 20, 2018.
International Search Report and Written Opinion dated Jul. 29, 2020 in PCT Application Serial No. PCT/US2020/034005.
International Search Report and Written Opinion dated Sep. 11, 2020 in PCT Application Serial No. PCT/US2020/038517.
International Search Report and Written Opinion dated Sep. 9, 2020 in PCT Application Serial No. PCT/US2020/038530.
International Search Report and Written Opinion dated Sep. 11, 2020 in PCT Application Serial No. PCT/US2020/038521.
International Search Report and Written Opinion dated Sep. 7, 2020 in PCT Application Serial No. PCT/US2020/034642.
International Preliminary Report on Patentability dated Sep. 15, 2020 in PCT Application Serial No. PCT/US2019/022009.
International Search Report and Written Opinion dated Sep. 14, 2020 in PCT Application Serial No. PCT/US2020/038523.
International Search Report and Written Opinion dated Oct. 2, 2020 in PCT Application Serial No. PCT/US2020/036107.
Schafter+Kirchhoff, Laser Beam Couplers series 60SMS for coupling into single-mode and polarization-maintaining fiber cables, Schafter+Kirchhoff, pp. 1-5, Germany. Dec. 2, 2021.
International Search Report and Written Opinion dated Jan. 29, 2020 in PCT Application Serial No. PCT/US2020/059961.
International Search Report and Written Opinion dated Jan. 20, 2020 in PCT Application Serial No. PCT/US2020/054792.
Partial Search Report and Provisional Opinion dated Feb. 19, 2021 in PCT Application Serial No. PCT/US2020/059960.
Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.
Nademanee, Koonlawee, et al. "A new approach for catheter ablation of atrial fibrillation: mapping of the electrophysiologic substrate." Journal of the American College of Cardiology 43.11 (2004): 2044-2053.
Calkins, Hugh. "Three dimensional mapping of atrial fibrillation: techniques and necessity." Journal of interventional cardiac electrophysiology 13.1 (2005): 53-59.
Shariat, Mohammad Hassan. Processing the intracardiac electrogram for atrial fibrillation ablation. Diss. Queen's University (Canada), 2016.
Meng et al., "Accurate Recovery of Atrial Endocardial Potential Maps From Non-contact Electrode Data." Auckland Bioengineering Institute. (ID 1421). May 2019.
Jiang et al., "Multielectrode Catheter for Substrate Mapping for Scar-related VT Ablation: A Comparison Between Grid Versus Linear Configurations." UChicago Medicine, Center for Arrhythmia Care, Chicago IL (ID 1368). Poster for conference in San Francisco, May 8-11, 2019.
Sacher et al., "Comparison of Manual Vs Automatic Annotation to Identify Abnormal Substrate for Scar Related VT Ablation." LIRYC

(56) References Cited

OTHER PUBLICATIONS

Institute, Bordeaux University Hospital, France (ID 1336). Poster for conference in San Francisco, May 8-11, 2019.
Oriel Instruments, "Introduction to Beam Splitters for Optical Research Applications", Apr. 2014, pp. 1-9, https://www.azoptics.com/Article.aspx?ArticaID=871.
International Search Report and Written Opinion dated Apr. 12, 2021 in PCT Application Serial No. PCT/US2020/059960.
International Search Report and Written Opinion dated Apr. 13, 2021 in PCT Application Serial No. PCT/US2020/064846.
International Search Report and Written Opinion dated Apr. 13, 2021 in PCT Application Serial No. PCT/US2021/013944.
International Search Report and Written Opinion dated May 25, 2021 in PCT Application Serial No. PCT/US2021/017604.
International Search Report and Written Opinion dated Jun. 2, 2021 in PCT Application Serial No. PCT/US2021/018522.
International Search Report and Written Opinion dated Jun. 2, 2021 in PCT Application Serial No. PCT/US2021/015204.
International Search Report and Written Opinion dated Jun. 17, 2021 in PCT Application Serial No. PCT/US2021/020934.
International Search Report and Written Opinion dated Jul. 13, 2021 in PCT Application Serial No. PCT/US2021/024216.
International Search Report and Written Opinion dated Jun. 22, 2021 in PCT Application Serial No. PCT/US2021/020937.
International Search Report and Written Opinion dated Jun. 24, 2021 in PCT Application Serial No. PCT/US2021/021272.
International Search Report and Written Opinion dated Aug. 20, 2021 in PCT Application Serial No. PCT/US2021/031130.
International Search Report and Written Opinion dated Apr. 4, 2022 in PCT Application Serial No. PCT/US2021/062170.
International Search Report and Written Opinion dated Apr. 4, 2022 in PCT Application Serial No. PCT/US2021/065073.
Partial Search Report and Provisional Opinion dated May 3, 2022 in PCT Application No. PCT/US2022/015577.
International Search Report and Written Opinion dated May 13, 2022 in PCT Application Serial No. PCT/US2022/017562.
International Search Report and Written Opinion dated Jun. 28, 2022, in PCT Application Serial No. PCT/US2022/015577.
International Search Report and Written Opinion dated Jun. 27, 2022, in PCT Application Serial No. PCT/US2022/022460.
International Search Report and Written Opinion dated Aug. 25, 2022 in PCT Application Serial No. PCT US/2022/028035.
International Search Report and Written Opinion dated Sep. 15, 2022 in PCT Application Serial No. PCT US/2022/032045.
International Search Report and Written Opinion dated Nov. 8, 2022 in PCT Application Serial No. PCT US/2022/039678.
International Search Report and Written Opinion, PCT Application Serial No. PCT/US2022/047751 issued Feb. 10, 2023, by the European Patent Office.
International Search Report and Written Opinion, PCT Application Serial No. PCT/US2022/047691 issued Feb. 13, 2023, by the European Patent Office.
AccuCoat, "Beamsplitter: Divide, combine & conquer"; 2023.
Lin et al., "Photoacoustic imaging", Science Direct; 2021.
Zhou et al., "Photoacoustic Imaging with fiber optic technology: A review", Science Direct; 2020.
International Search Report and Written Opinion issued by the European Patent Office, for Serial No. PCT/US2022/053775, dated Apr. 21, 2023.
International Search Report and Written Opinion issued by the European Patent Office, for Serial No. PCT/US2023/011497, dated Apr. 28, 2023.
International Search Report and Written Opinion issued by the European Patent Office, for Serial No. PCT/US2023/012599, dated May 19, 2023.
PathFinder Digital, "Free Space Optics vs. Fiber Optics", 2023.
International Search Report and Written Opinion, issued in Application Serial No. PCT/US2023/016152, dated Jul. 12, 2023.
Definition of ablation—NCI Dictionary of Cancer Terms—NCI, National Cancer Institute, p. 1 (Year:2025).
Daemen, J., Tovar Forero, M.N, "The Coronary Intravascular Lithotripsy System", ICR Journal, 2019; 14(3); 174-181.
Butt, N., Khalid, N., Shlofmitz, E., "Intravascular Lithotripsy"; NCBI Bookshelf. A service of the National Library of Medicine, National Institutes of Health; StatPearls Publishing, 2023.

* cited by examiner

CATHETER INFLATION TUBE FOR USE IN INTRAVASCULAR LITHOTRIPSY

RELATED APPLICATION

This Application is related to and claims priority on U.S. Provisional Patent Application Ser. No. 63/334,553 filed on Apr. 25, 2022, and entitled "CATHETER INFLATION TUBE FOR USE IN INTRAVASCULAR LITHOTRIPSY." To the extent permissible, the contents of U.S. Provisional Application Ser. No. 63/334,553 are incorporated in its entirety herein by reference.

BACKGROUND

Vascular lesions within vessels in the body can be associated with an increased risk for major adverse events, such as myocardial infarction, embolism, deep vein thrombosis, stroke, and the like. Severe vascular lesions can be challenging to treat and achieve patency for a physician in a clinical setting. Vascular lesions may be treated using interventions such as drug therapy, balloon angioplasty, atherectomy, stent placement, and vascular graft bypass, to name a few. Such interventions may not always be ideal or may require subsequent treatment intravascular lithotripsy to address the lesion.

Angioplasty catheters used to treat calcified arteries can have a common problem with removing air from the balloon during an intravascular lithotripsy balloon procedure. Techniques, such as a pulling vacuum with a manual pump within the catheter prior to media inflation, can be employed to minimize air volume inside the balloon. Consequently, despite this vacuum method, post-media inflation, there can be a small amount of air inside the balloon. The air inside the balloon is problematic for intravascular lithotripsy balloon catheters because it can impede the catheter's ability to generate a pressure wave, therefore reducing energy delivery.

Additionally, gas bubbles can accumulate throughout the intravascular lithotripsy balloon procedure as more energy applications are delivered inside the balloon. The disadvantage of adding a separate irrigation lumen is that it adds additional diameter to the crossing profile of the balloon. The larger the crossing profile, the more difficult it is for the physician to cross severely calcified vessels. Balloons with crossing profiles larger than the stenosed vessel will not be able to track through the lesion without intervention from devices that can create a pathway big enough for the balloon. It can be challenging to generate enough flow through small ports without high pressure and without making the central lumen large and thereby increasing the crossing profile of the balloon. It can also be difficult to (i) manufacture the extrusion at a small size and (ii) create a seal that can withstand high pressure to achieve flow.

SUMMARY

The present invention is directed toward a catheter system for treating a treatment site within or adjacent to a vessel wall or a heart valve. In various embodiments, the catheter system includes a balloon and an inflation tube. The balloon has a balloon interior. The inflation tube is configured to guide a flow of an inflation fluid into the balloon interior, The inflation tube has an inflation lumen. The inflation tube is movable between (i) an open configuration wherein the inflation lumen has a first cross-sectional area, and (ii) a collapsed configuration wherein the inflation lumen has a second cross-sectional area that is less than the first cross-sectional area.

In various embodiments, the inflation tube is biased toward the collapsed configuration.

In some embodiments, the inflation tube is configured to be moved to the open configuration using fluid pressure.

In certain embodiments, the inflation tube is biased toward the open configuration.

In various embodiments, the inflation tube is at least partially formed from one of a polymer, a plastic, a synthetic material and a natural material.

In some embodiments, the inflation tube includes a tube wall that varies in thickness.

In certain embodiments, the inflation tube is fully collapsible so that the second cross-sectional area of the inflation lumen is approximately equal to zero.

In various embodiments, in the collapsed configuration, a cross-sectional shape of the inflation tube is substantially elliptical.

In some embodiments, in the open configuration, a cross-sectional shape of the inflation tube is substantially circular.

In certain embodiments, the inflation tube includes a tube adhesive so that the inflation tube is adherable to itself when the inflation tube is in the collapsed configuration.

In various embodiments, the inflation tube has a tube length, and the inflation tube is configured to move to the collapsed configuration along at least a portion of the tube length.

In some embodiments, the inflation tube has a tube length, and the inflation tube is thermally formed along at least a portion of the tube length.

In certain embodiments, the inflation tube is at least partially formed from a first polymer and a second polymer that is different than the first polymer. In some embodiments, the first polymer and the second polymer are thermally bonded to one another.

In various embodiments, the inflation tube includes one or more thermal bonds that are configured to fuse extrusions of varying polymers that at least partially form the inflation tube.

In some embodiments, the second cross-sectional area is less than 90% of the first cross-sectional area.

In certain embodiments, the second cross-sectional area is less than 50% of the first cross-sectional area.

In various embodiments, the second cross-sectional area is less than 25% of the first cross-sectional area.

In some embodiments, the catheter system includes (i) an energy source that generates energy, and (ii) an energy guide that guides the energy into the balloon to generate a plasma to create pressure waves within the balloon interior near the treatment site.

In certain embodiments, the energy source includes a laser, and the energy guide includes an optical fiber.

In various embodiments, the energy guide includes an electrode pair including spaced apart electrodes that extend into the balloon interior. In some embodiments, pulses of high voltage from the energy source are applied to the electrodes and form an electrical arc across the electrodes to generate a plasma within the balloon interior.

The present invention is still further directed toward a method for treating a treatment site within or adjacent to a vessel wall or a heart valve comprising the step of providing any of the catheter systems described herein.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DESCRIPTION

Treatment of vascular lesions (also sometimes referred to herein as "treatment sites") can reduce major adverse events or death in affected subjects. As referred to herein, a major adverse event is one that can occur anywhere within the body due to the presence of a vascular lesion. Major adverse events can include but are not limited to, major adverse cardiac events, major adverse events in the peripheral or central vasculature, major adverse events in the brain, major adverse events in the musculature, or major adverse events in any of the internal organs.

As used herein, the terms "intravascular lesion," "vascular lesion," and "treatment site" are used interchangeably unless otherwise noted. The intravascular lesions and/or the vascular lesions are sometimes referred to herein simply as "lesions." Also, as used herein, the terms "focused location" and "focused spot" can be used interchangeably unless otherwise noted and can refer to any location where the light energy is focused to a small diameter than the initial diameter of the energy source.

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention, as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is appreciated that such a development effort might be complex and time-consuming. However, it would nevertheless be a routine undertaking of engineering for those of ordinary skill in the art having the benefit of this disclosure.

Figure 1:
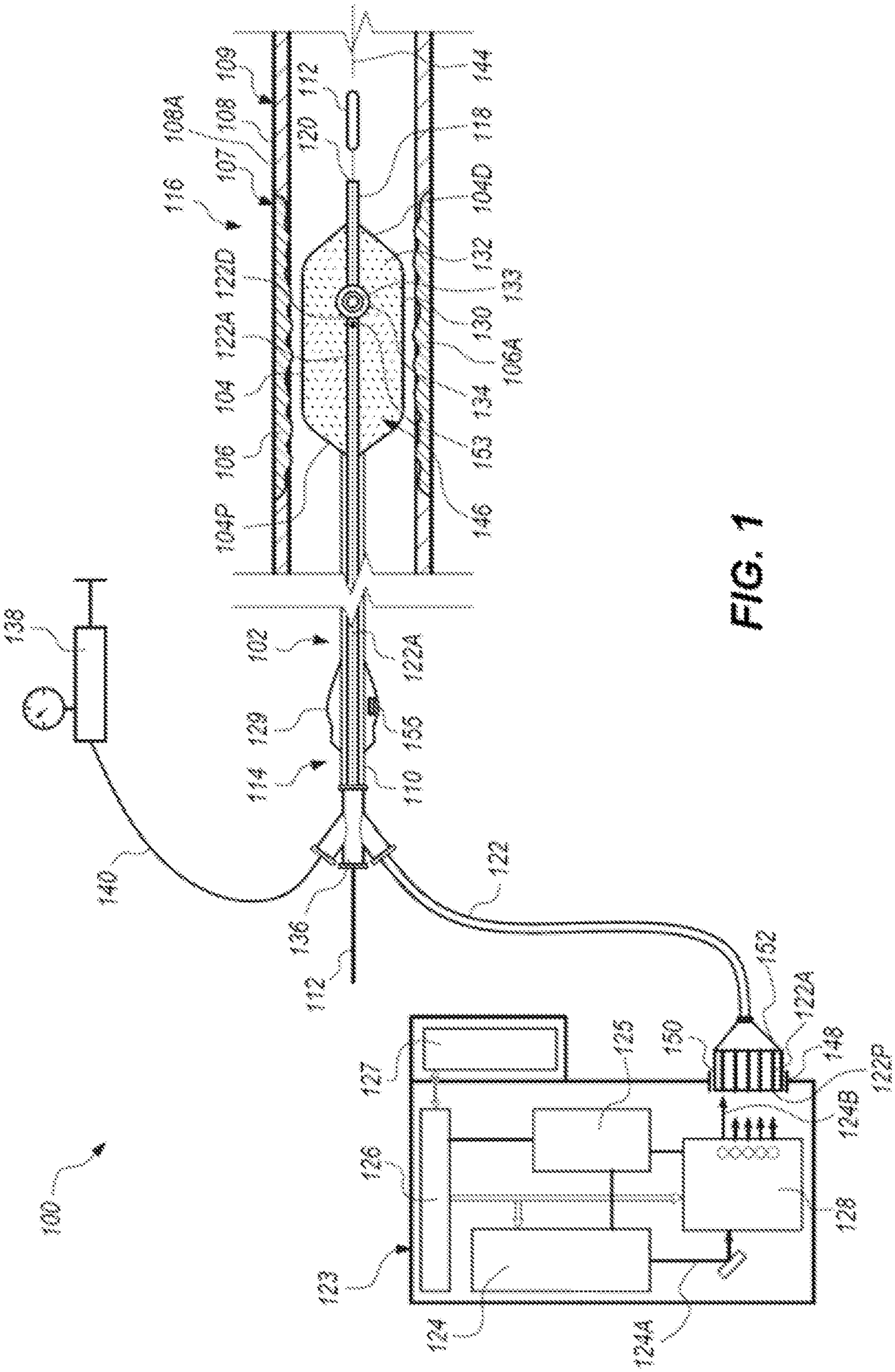
FIG. 1 is a simplified schematic diagram of one embodiment of a portion of a catheter system having features of the present invention.

It is appreciated that the catheter systems disclosed herein can include many different forms. Referring now to FIG. 1, a schematic cross-sectional view is shown of a catheter system 100 in accordance with various embodiments herein. As described herein, the catheter system 100 is suitable for imparting pressure to induce fractures in one or more treatment sites within or adjacent to a vessel wall of a blood vessel or heart valve within a body of a patient. In the embodiment illustrated in FIG. 1, the catheter system 100 can include one or more of a catheter 102, an energy guide bundle 122 including one or more energy guides 122A, a system console 123 including one or more of an energy source 124, a power source 125, a system controller 126, a graphic user interface 127 (a "GUI"), a multiplexer 128, a handle assembly 129, a source manifold 136, and a fluid pump 138. Alternatively, the catheter system 100 can include more components or fewer components than those specifically illustrated in FIG. 1.

In various embodiments, the catheter 102 is configured to move to a treatment site 106 within or adjacent to a vessel wall 108A of a blood vessel 108 within a body 107 of a patient 109. The treatment site 106 can include one or more vascular lesions 106A, such as calcified vascular lesions, for example. Additionally, or in the alternative, the treatment site 106 can include vascular lesions 106A, such as fibrous vascular lesions. Still alternatively, in some implementations, the catheter 102 can be used at a treatment site 106 within or adjacent to a heart valve within the body 107 of the patient 109.

The catheter 102 can include an inflatable balloon 104 (sometimes referred to herein simply as a "balloon"), a catheter shaft 110, and a guidewire 112. The balloon 104 can be coupled to the catheter shaft 110. The balloon 104 can include a balloon proximal end 104P and a balloon distal end 104D. The catheter shaft 110 can extend from a proximal portion 114 of the catheter system 100 to a distal portion 116 of the catheter system 100. The catheter shaft 110 can include a longitudinal axis 144. The catheter shaft 110 can also include a guidewire lumen 118, which is configured to move over the guidewire 112. As utilized herein, the guidewire lumen 118 defines a conduit through which the guidewire 112 extends. In some embodiments, the catheter 102 can have a distal end opening 120 and can accommodate and be tracked over the guidewire 112 as the catheter 102 is moved and positioned at or near the treatment site 106. In some embodiments, the balloon proximal end 104P can be coupled to the catheter shaft 110, and the balloon distal end 104D can be coupled to the guidewire lumen 118.

The balloon 104 includes a balloon wall 130 that defines a balloon interior 146. The balloon 104 can be selectively inflated with a inflation fluid 132 to expand from a deflated state, suitable for advancing the catheter 102 through a patient's vasculature, to an inflated state (as shown in FIG. 1) suitable for anchoring the balloon 104 in position relative to the treatment site 106. Stated in another manner, when the balloon 104 is in the inflated state, the balloon wall 130 of the balloon 104 is configured to be positioned substantially adjacent to and/or in contact with the treatment site 106. It is appreciated that although FIG. 1 illustrates the balloon wall 130 of the balloon 104 is shown spaced apart from the treatment site 106 of the blood vessel 108 when in the inflated state, this is done merely for ease of illustration. It is recognized that the balloon wall 130 of the balloon 104 will typically be substantially in contact with and/or directly adjacent to the treatment site 106 when the balloon 104 is in the inflated state.

The balloon 104 suitable for use in the catheter system 100 includes those that can be passed through the vasculature of a patient 109 when in the deflated state. In some embodiments, the balloon 104 is made from silicone. In other embodiments, the balloon 104 can be made from polydimethylsiloxane (PDMS), polyurethane, polymers such as PEBAX™ material, nylon, as non-exclusive examples, or any other suitable material.

The balloon 104 can have any suitable diameter (in the inflated state). In various embodiments, the balloon 104 can have a diameter (in the inflated state) ranging from less than one millimeter (mm) up to 25 mm. In some embodiments, the balloon 104 can have a diameter (in the inflated state) ranging from at least 1.5 mm up to 14 mm. In some embodiments, the balloon 104 can have a diameter (in the inflated state) ranging from at least two mm up to five mm.

In some embodiments, the balloon 104 can have a length ranging from at least three mm to 300 mm. More particularly, in some embodiments, the balloon 104 can have a length ranging from at least eight mm to 200 mm. It is appreciated that a balloon 104 having a relatively longer length can be positioned adjacent to larger treatment sites 106, and, thus, may be used for imparting pressure waves onto and inducing fractures in larger vascular lesions 106A or multiple vascular lesions 106A at precise locations within the treatment site 106. It is further appreciated that a longer balloon 104 can also be positioned adjacent to multiple treatment sites 106 at any one given time.

The balloon 104 can be inflated to inflation pressures of between approximately one atmosphere (atm) and 70 atm. In some embodiments, the balloon 104 can be inflated to inflation pressures of from at least 20 atm to 60 atm. In other embodiments, the balloon 104 can be inflated to inflation pressures of from at least six atm to 20 atm. In still other embodiments, the balloon 104 can be inflated to inflation pressures of from at least three atm to 20 atm. In yet other embodiments, the balloon 104 can be inflated to inflation pressures of from at least two atm to ten atm.

The inflation fluid 132 can be a liquid or a gas. Some examples of the inflation fluid 132 suitable for use can include, but are not limited to, one or more of water, saline, contrast medium, fluorocarbons, perfluorocarbons, gases, such as carbon dioxide, or any other suitable inflation fluid 132. In some embodiments, the inflation fluid 132 can be used as a base inflation fluid. In some embodiments, the inflation fluid 132 can include a mixture of saline to contrast medium in a volume ratio of approximately 50:50. In other embodiments, the inflation fluid 132 can include a mixture of saline to contrast medium in a volume ratio of approximately 25:75. In still other embodiments, the inflation fluid 132 can include a mixture of saline to contrast medium in a volume ratio of approximately 75:25. However, it is understood that any suitable ratio of saline to contrast medium can be used. The inflation fluid 132 can be tailored on the basis of composition, viscosity, and the like so that the rate of travel of the pressure waves are appropriately manipulated. In certain embodiments, the inflation fluid 132 suitable for use herein is biocompatible. A volume of inflation fluid 132 can be tailored by the chosen energy source 124 and the type of inflation fluid 132 used.

In some embodiments, the contrast agents used in the contrast media can include but are not limited to iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine-based contrast agents can be used. Suitable non-iodine-containing contrast agents can include gadolinium (III)-based contrast agents. Suitable fluorocarbon and perfluorocarbon agents can include, but are not limited to, agents such as perfluorocarbon dodecafluoropentane (DDFP, C5F12).

The inflation fluids 132 can include those that include absorptive agents that can selectively absorb light in the ultraviolet region (e.g., at least ten nanometers (nm) to 400 nm), the visible region (e.g., at least 400 nm to 780 nm), or the near-infrared region (e.g., at least 780 nm to 2.5 μm) of the electromagnetic spectrum. Suitable absorptive agents can include those with absorption maxima along the spectrum from at least ten nm to 2.5 μm. Alternatively, the inflation fluid 132 can include absorptive agents that can selectively absorb light in the mid-infrared region (e.g., at least 2.5 μm to 15 μm) or the far-infrared region (e.g., at least 15 μm to one mm) of the electromagnetic spectrum. In various embodiments, the absorptive agent can be those that have an absorption maximum matched with the emission maximum of the laser used in the catheter system 100. By way of non-limiting examples, various lasers described herein can include neodymium:yttrium-aluminum-garnet (Nd:YAG—emission maximum=1064 nm) lasers, holmium:YAG (Ho:YAG—emission maximum=2.1 μm) lasers, or erbium:YAG (Er:YAG—emission maximum=2.94 μm) lasers. In some embodiments, the absorptive agents can be water-soluble. In other embodiments, the absorptive agents are not water-soluble. In some embodiments, the absorptive agents used in the inflation fluids 132 can be tailored to match the peak emission of the energy source 124. Various energy sources 124 having emission wavelengths of at least ten nanometers to one millimeter are discussed elsewhere herein.

The catheter shaft 110 of the catheter 102 can be coupled to the one or more energy guides 122A of the energy guide bundle 122 that are in optical and/or electrical communication with the energy source 124. The energy guide(s) 122A can be disposed along the catheter shaft 110 and within the balloon 104. Each of the energy guides 122A can have a guide distal end 122D that is at any suitable longitudinal position relative to a length of the balloon 104. In some embodiments, each energy guide 122A can include an optical fiber, and the energy source 124 can be a laser. Alternatively, the energy guide 122A can include one or more electrodes, and the energy source 124 can include a high voltage generator. The energy source 124 can be in optical and/or electrical communication with the energy guides 122A at the proximal portion 114 of the catheter system 100. More particularly, the energy source 124 can selectively, simultaneously, and/or sequentially be in optical and/or electrical communication with each of the energy guides 122A in any desired combination, order, and/or pattern.

In some embodiments, the catheter shaft 110 can be coupled to multiple energy guides 122A, such as a first energy guide, a second energy guide, a third energy guide, etc., which can be disposed at any suitable position about the guidewire lumen 118 and/or the catheter shaft 110. For example, in certain non-exclusive embodiments, two energy guides 122A can be spaced apart by approximately 180 degrees about the circumference of the guidewire lumen 118 and/or the catheter shaft 110; three energy guides 122A can be spaced apart by approximately 120 degrees about the circumference of the guidewire lumen 118 and/or the catheter shaft 110, or four energy guides 122A can be spaced apart by approximately 90 degrees about the circumference of the guidewire lumen 118 and/or the catheter shaft 110, etc. Still alternatively, multiple energy guides 122A need not be uniformly spaced apart from one another about the circumference of the guidewire lumen 118 and/or the catheter shaft 110. More particularly, the energy guides 122A can be disposed either uniformly or non-uniformly about the guidewire lumen 118 and/or the catheter shaft 110 to achieve the desired effect in the desired locations.

The energy guide bundle 122 can include any number of energy guides 122A in optical communication with the energy source 124 at the proximal portion 114, and with the inflation fluid 132 within the balloon interior 146 of the balloon 104 at the distal portion 116. For example, in some embodiments, the catheter system 100 and/or the energy guide bundle 122 can include from one energy guide 122A to five energy guides 122A. In other embodiments, the catheter system 100 and/or the energy guide bundle 122 can include from five energy guides 122A to fifteen energy guides 122A. In yet other embodiments, the catheter system 100 and/or the energy guide bundle 122 can include from ten energy guides 122A to thirty energy guides 122A. Alternatively, in still other embodiments, the catheter system 100 and/or the energy guide bundle 122 can include greater than 30 energy guides 122A.

The energy guide bundle 122 can also include a guide bundler 152 that brings each of the individual energy guides 122A closer together so that the energy guides 122A and/or the energy guide bundle 122 can be in a more compact form as it extends along or inside the catheter 102 into the blood vessel 108 during use of the catheter system 100. In some embodiments, the energy guides 122A leading to the plasma generator 133 can be organized into the energy guide bundle 122, including a linear block with an array of precision holes forming a multi-channel ferrule. In other embodiments, the energy guide bundle 122 can include a mechanical connector array or block connector that organizes singular ferrules into one of (i) a linear array, (ii) a circular pattern, and (iii) a hexagonal pattern. Alternatively, the energy guide bundle 122 can include a mechanical connector array or block connector that organizes singular ferrules into another suitable array or pattern.

The energy guides 122A can have any suitable design for the purposes of generating plasma and/or pressure waves in the inflation fluid 132 within the balloon interior 146. In certain embodiments, the energy guides 122A can include an optical fiber or flexible light pipe. The energy guides 122A can be thin and flexible and can allow light signals to be sent with very little loss of strength. The energy guides 122A can include a core surrounded by a cladding about its circumference. In some embodiments, the core can be a cylindrical core or a partially cylindrical core. The core and cladding of the energy guides 122A can be formed from one or more materials, including but not limited to one or more types of glass, silica, or one or more polymers. The energy guides 122A may also include a protective coating, such as a polymer. It is appreciated that the index of refraction of the core will be greater than the index of refraction of the cladding.

Each energy guide 122A can guide light energy along its length from a guide proximal end 122P to the guide distal end 122D, having at least one optical window (not shown) that is positioned within the balloon interior 146.

The energy guides 122A can assume many configurations about and/or relative to the catheter shaft 110 of the catheter 102. In some embodiments, the energy guides 122A can run parallel to the longitudinal axis 144 of the catheter shaft 110. In some embodiments, the energy guides 122A can be physically coupled to the catheter shaft 110. In other embodiments, the energy guides 122A can be disposed along a length of an outer diameter of the catheter shaft 110. In yet other embodiments, the energy guides 122A can be disposed within one or more energy guide lumens within the catheter shaft 110.

The energy guides 122A can also be disposed at any suitable positions about the circumference of the guidewire lumen 118 and/or the catheter shaft 110, and the guide distal end 122D of each of the energy guides 122A can be disposed at any suitable longitudinal position relative to the length of the balloon 104 and/or relative to the length of the guidewire lumen 118 to more effectively and precisely impart pressure waves for purposes of disrupting the vascular lesions 106A at the treatment site 106.

In certain embodiments, the energy guides 122A can include one or more photoacoustic transducers 153. Each photoacoustic transducer 153 can be in optical communication with the energy guide 122A within which it is disposed. In some embodiments, the photoacoustic transducers 153 can be in optical communication with the guide distal end 122D of the energy guide 122A. Additionally, in such embodiments, the photoacoustic transducers 153 can have a shape that corresponds with and/or conforms to the guide distal end 122D of the energy guide 122A. Alternatively, no photoacoustic transducers 153 may be included.

The photoacoustic transducer 153 is configured to convert light energy into an acoustic wave at or near the guide distal end 122D of the energy guide 122A. The direction of the acoustic wave can be tailored by changing an angle of the guide distal end 122D of the energy guide 122A.

In certain embodiments, the photoacoustic transducers 153 disposed at the guide distal end 122D of the energy guide 122A can assume the same shape as the guide distal end 122D of the energy guide 122A. For example, in certain non-exclusive embodiments, the photoacoustic transducer 153 and/or the guide distal end 122D can have a conical shape, a convex shape, a concave shape, a bulbous shape, a square shape, a stepped shape, a half-circle shape, an ovoid shape, and the like. The energy guide 122A can further include additional photoacoustic transducers 153 disposed along one or more side surfaces of the length of the energy guide 122A.

In some embodiments, the energy guides 122A can further include one or more diverting features or "diverters" (not shown in FIG. 1) within the energy guide 122A that are configured to direct light to exit the energy guide 122A toward a side surface which can be located at or near the guide distal end 122D of the energy guide 122A, and toward the balloon wall 130. A diverting feature can include any system feature that diverts light energy from the energy guide 122A away from its axial path toward a side surface of the energy guide 122A. Additionally, the energy guides 122A can each include one or more light windows disposed along the longitudinal or circumferential surfaces of each energy guide 122A and in optical communication with a diverting feature. Stated in another manner, the diverting features can be configured to direct light energy in the energy guide 122A toward a side surface that is at or near the guide distal end 122D, where the side surface is in optical communication with a light window. The light windows can include a portion of the energy guide 122A that allows light energy to exit the energy guide 122A from within the energy guide 122A, such as a portion of the energy guide 122A lacking a cladding material on or about the energy guide 122A.

Examples of the diverting features suitable for use include a reflecting element, a refracting element, and a fiber diffuser. The diverting features suitable for focusing light energy away from the tip of the energy guides 122A can include but are not to be limited to, those having a convex surface, a gradient-index (GRIN) lens, and a mirror focus lens. Upon contact with the diverting feature, the light energy is diverted within the energy guide 122A to one or more of a plasma generator 133 and the photoacoustic transducer 153 that is in optical communication with a side surface of the energy guide 122A. As noted, the photoacoustic transducer 153 then converts light energy into an acoustic wave that extends away from the side surface of the energy guide 122A.

In the embodiment illustrated in FIG. 1, the system console 123 can include one or more of the light source 124, the power source 125, the system controller 126, the GUI 127, and/or the multiplexer 128. Alternatively, the system console 123 can include more components or fewer components than those specifically illustrated in FIG. 1. For example, in certain non-exclusive alternative embodiments, the system console 123 can be designed without the GUI 127. Still alternatively, one or more of the energy source 124, the power source 125, the system controller 126, the GUI 127, and the multiplexer 128 can be included within the catheter system 100 without the specific need for the system console 123.

Additionally, as shown, the system console 123, and the components included therewith, is operatively coupled to the catheter 102, the energy guide bundle 122, and the remainder of the catheter system 100. For example, in some embodiments, as illustrated in FIG. 1, the system console 123 can include a console connection aperture 148, via which the energy guide bundle 122 is mechanically coupled to the system console 123. In such embodiments, the energy guide bundle 122 can include a guide coupling housing 150 (also sometimes referred to herein as a "ferrule") that houses a portion, e.g., the guide proximal end 122P, of each of the energy guides 122A. The guide coupling housing 150 is configured to fit and be selectively retained within the console connection aperture 148 to provide the desired mechanical coupling between the energy guide bundle 122 and the system console 123.

The energy source 124 can be selectively and/or alternatively coupled in optical communication with each of the energy guides 122A, i.e., to the guide proximal end 122P of each of the energy guides 122A, in the energy guide bundle 122 so that the guide proximal end 122P is electrically and/or optically coupled to the energy source 124. In particular, the energy source 124 can be configured to generate energy (such as light energy or electrical energy, in certain embodiments) in the form of a source beam 124A, such as a pulsed source beam, that can be selectively and/or alternatively directed to and received by each of the energy guides 122A in the energy guide bundle 122 as an individual guide beam 124B. In certain embodiments, the energy emitted by the energy source 124, such as the source beam 124A and the individual guide beam 124B, can be concentrated to transmit through a long, narrow medium (such as the energy guides 122A) to bring it from the energy source 124 to the plasma generator 133 so that the plasma generator 133 can generate highly localized mechanical effects to treat localized lesions (e.g., the treatment site 106). Various embodiments of the catheter system 100 described herein have improved efficacy for use in narrow human anatomy such as blood vessels 108.

Alternatively, the catheter system 100 can include more than one energy source 124. For example, in one non-exclusive alternative embodiment, the catheter system 100 can include a separate energy source 124 for each energy guide 122A in the energy guide bundle 122. The energy source 124 can be operated at low energies. In other embodiments, the energy source 124 can be electrical, such as a high-voltage pulse generator.

The energy source 124 can have any suitable design. In certain embodiments, the energy source 124 can be configured to provide sub-millisecond pulses of light energy from the energy source 124 that are focused onto a small spot in order to couple it into the guide proximal end 122P of the energy guide 122A. Such pulses of light energy are then directed and/or guided along the energy guides 122A to a location within the balloon interior 146 of the balloon 104, thereby inducing plasma formation in the inflation fluid 132 within the balloon interior 146 of the balloon 104, such as via the plasma generator 133 that can be located at the guide distal end 122D of the energy guide 122A. By locating the plasma generator 133 at the guide distal end 122D, the plasma generator 133 can be routed through torturous human anatomy, such as a constricted artery, for placement adjacent to the treatment site 106. In some embodiments, the plasma generator 133 can be at least partially formed by a metal. In various embodiments, the plasma generator 133 can be configured to be immersed in a liquid (e.g., the inflation fluid 132) that converts the plasma into a mechanical acoustic bubble and transports this energy to the treatment site 106.

In particular, the light emitted at the guide distal end 122D of the energy guide 122A energizes the plasma generator 133 to form the plasma within the inflation fluid 132 within the balloon interior 146. The plasma formation causes rapid bubble formation and imparts pressure waves upon the treatment site 106. An exemplary plasma-induced bubble 134 is illustrated in FIG. 1.

In various non-exclusive alternative embodiments, sub-millisecond pulses of light energy from the energy source 124 can be delivered to the treatment site 106 at a frequency of between approximately one hertz (Hz) and 5000 Hz, between approximately 30 Hz and 1000 Hz, between approximately ten Hz and 100 Hz, or between approximately one Hz and 30 Hz. Alternatively, the sub-millisecond pulses of light energy can be delivered to the treatment site 106 at a frequency that can be greater than 5000 Hz or less than one Hz or any other suitable range of frequencies.

It is appreciated that although the energy source 124 can be utilized to provide pulses of light energy, the energy source 124 can still be described as providing a single source beam 124A, i.e., a single pulsed source beam, or another suitable type of energy source such as a high voltage pulse generator.

Some energy sources 124 suitable for use can include various types of energy sources, including lasers, seed sources, and lamps. For example, in certain non-exclusive embodiments, the energy source 124 can be an infrared laser that emits light energy in the form of pulses of infrared light. Alternatively, as noted above, the energy sources 124, as referred to herein, can include any other suitable type of energy source.

Suitable lasers can include short pulse lasers on the sub-millisecond timescale. In some embodiments, the energy source 124 can include lasers on the nanosecond (ns) timescale. The lasers can also include short pulse lasers on the picosecond (ps), femtosecond (fs), and microsecond (us) timescales. It is appreciated that there are many combinations of laser wavelengths, pulse widths, and energy levels that can be employed to achieve plasma in the inflation fluid 132 of the catheter 102. In various non-exclusive alternative embodiments, the pulse widths can include those falling within a range, including at least ten ns to 3000 ns, at least 20 ns to 100 ns, or at least one ns to 500 ns. Alternatively, any other suitable pulse width range can be used.

Exemplary nanosecond lasers can include those within the UV to IR spectrum, spanning wavelengths of about ten nanometers (nm) to one millimeter (mm). In some embodiments, the energy sources 124 suitable for use in the catheter system 100 can include those capable of producing light at wavelengths of from at least 750 nm to 2000 nm. In other embodiments, the energy sources 124 can include those capable of producing light at wavelengths of from at least 700 nm to 3000 nm. In still other embodiments, the energy sources 124 can include those capable of producing light at wavelengths of from at least 100 nm to ten micrometers (μm). Nanosecond lasers can include those having repetition rates of up to 200 kHz. In some embodiments, the laser can include a Q-switched thulium:yttrium-aluminum-garnet (Tm:YAG) laser. In other embodiments, the laser can include a neodymium:yttrium-aluminum-garnet (Nd:YAG) laser, holmium:yttrium-aluminum-garnet (Ho:YAG) laser, erbium:yttrium-aluminum-garnet (Er:YAG) laser, excimer laser, helium-neon laser, carbon dioxide laser, as well as doped, pulsed, fiber lasers. In still further embodiments, the energy source 124 can include SLEDs that have bandwidths ranging from 13.25 GHz to 18.25 GHz at 1064 nm.

The catheter system 100 can generate pressure waves having maximum pressures in the range of at least one megapascal (MPa) to 100 MPa. The maximum pressure generated by a particular catheter system 100 will depend on the energy source 124, the absorbing material, the bubble expansion, the propagation medium, the balloon material, and other factors. In various non-exclusive alternative embodiments, the catheter system 100 can generate pressure waves having maximum pressures in the range of at least approximately two MPa to 50 MPa, at least approximately two MPa to 30 MPa, or at least approximately 15 MPa to 25 MPa.

The pressure waves can be imparted upon the treatment site 106 from a distance within a range from at least approximately 0.1 millimeters (mm) to greater than approximately 25 mm, extending radially from the energy guides 122A when the catheter 102 is placed at the treatment site 106. In various non-exclusive alternative embodiments, the pressure waves can be imparted upon the treatment site 106 from a distance within a range from at least approximately ten mm to 20 mm, at least approximately one mm to ten mm, at least approximately 1.5 mm to four mm, or at least approximately 0.1 mm to ten mm extending radially from the energy guides 122A when the catheter 102 is placed at the treatment site 106. In other embodiments, the pressure waves can be imparted upon the treatment site 106 from another suitable distance that is different than the foregoing ranges. In some embodiments, the pressure waves can be imparted upon the treatment site 106 within a range of at least approximately two MPa to 30 MPa at a distance from at least approximately 0.1 mm to ten mm. In some embodiments, the pressure waves can be imparted upon the treatment site 106 from a range of at least approximately two MPa to 25 MPa at a distance from at least approximately 0.1 mm to ten mm. Still alternatively, other suitable pressure ranges and distances can be used.

The power source 125 is electrically coupled to and is configured to provide the necessary power to one or more of the energy source 124, the system controller 126, the GUI 127, and the handle assembly 129. The power source 125 can have any suitable design for such purposes.

The system controller 126 is electrically coupled to and receives power from the power source 125. Additionally, the system controller 126 is coupled to and is configured to control the operation of each of the energy sources 124, and the GUI 127. The system controller 126 can include one or more processors or circuits for purposes of controlling the operation of at least the energy source 124, and the GUI 127. For example, the system controller 126 can control the energy source 124 for generating pulses of light energy as desired and/or at any desired firing rate.

The system controller 126 can further be configured to control the operation of other components of the catheter system 100, such as the positioning of the catheter 102 adjacent to the treatment site 106, the inflation of the balloon 104 with the inflation fluid 132, etc. Further, or in the alternative, the catheter system 100 can include one or more additional controllers that can be positioned in any suitable manner for the purposes of controlling the various operations of the catheter system 100. For example, in certain embodiments, an additional controller and/or a portion of the system controller 126 can be positioned and/or incorporated within the handle assembly 129.

In some embodiments, the multiplexer 128 can include a two-channel splitter design. The guide bundle 122 can include a manual positioning mechanism that is mounted on an optical breadboard and/or platen. This design enables linear positional adjustment and array tilting by rotating about a Channel 1 energy guide 122A axis (not shown in FIG. 1). The adjustment method, in other embodiments, can include at least two adjustment steps, 1) aligning the planar positions of the source beam 124A at Channel 1, and 2) adjusting the energy guide bundle 122 to achieve the best alignment at Channel 10.

As shown in FIG. 1, the handle assembly 129 can be positioned at or near the proximal portion 114 of the catheter system 100, and/or near the source manifold 136. In this embodiment, the handle assembly 129 is coupled to the balloon 104 and is positioned spaced apart from the balloon 104. Alternatively, the handle assembly 129 can be positioned at another suitable location.

The handle assembly 129 is handled and used by the user or operator to operate, position, and control the catheter 102. The design and specific features of the handle assembly 129 can vary to suit the design requirements of the catheter system 100. In the embodiment illustrated in FIG. 1, the handle assembly 129 is separate from, but in electrical, optical, and/or fluid communication with one or more of the system controller 126, the energy source 124, the GUI 127 and/or the fluid pump 138. In some embodiments, the handle assembly 129 can integrate and/or include at least a portion of the system controller 126 within an interior of the handle assembly 129. For example, as shown, in certain such embodiments, the handle assembly 129 can include circuitry 155 that can form at least a portion of the system controller 126.

In one embodiment, the circuitry 155 can include a printed circuit board having one or more integrated circuits, or any other suitable circuitry. In an alternative embodiment, the circuitry 155 can be omitted or can be included within the system controller 126 or otherwise within the system console 123, which in various embodiments can be positioned outside of the handle assembly 129.

The source manifold 136 can be positioned at or near the proximal portion 114 of the catheter system 100. The source manifold 136 can include one or more proximal end openings that can receive the one or more energy guides 122A of the energy guide bundle 122, the guidewire 112, and/or an inflation conduit 140 that is coupled in fluid communication with the fluid pump 138.

The fluid pump 138 is configured to inflate the balloon 104 with the inflation fluid 132 as needed.

Figure 2:
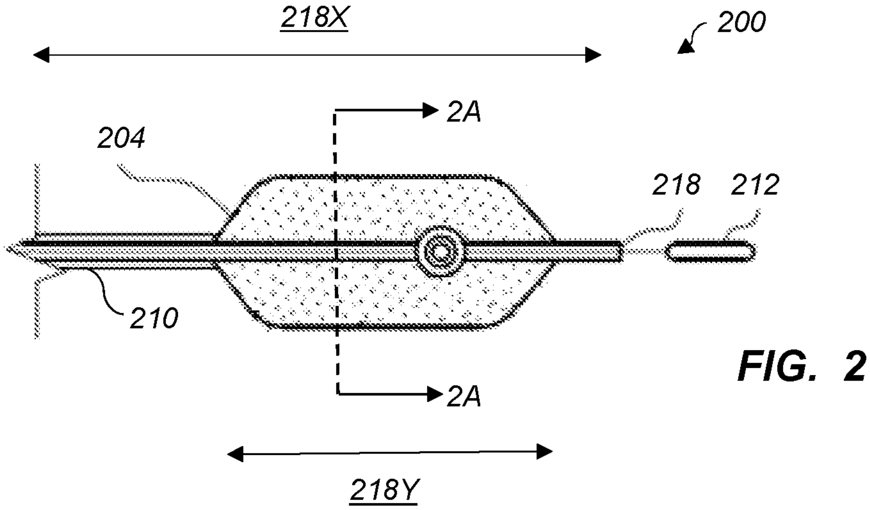
FIG. 2 is a simplified schematic diagram of another embodiment of a portion of the catheter system.

FIG. 2 is a simplified schematic diagram of another embodiment of a portion of the catheter system 200. As shown in FIG. 2, the catheter system 200 can include an inflatable balloon 204, a catheter shaft 210, a guidewire 212, and/or a guidewire lumen 218, having a first length 218X and a second length 218Y. The first length 218X can include the entirety of the guidewire lumen 218, and the second length 218Y can include the portion of the guidewire lumen 218 that is located in the balloon interior 146 (illustrated in FIG. 1) of the balloon 204.

Figure 2A:
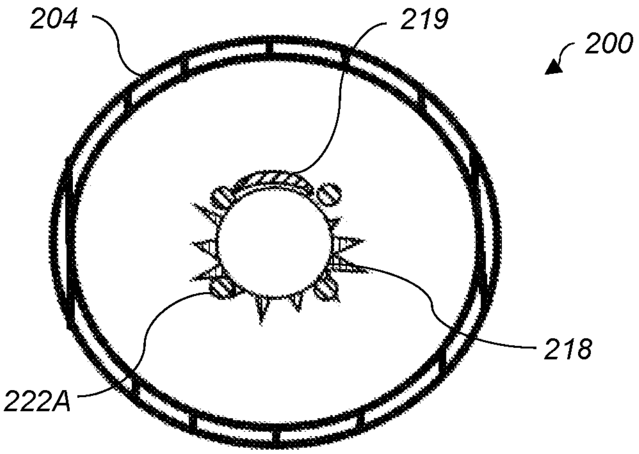
FIG. 2A is a simplified cross-sectional view taken on line 2A-2A in FIG. 2, including an inflation tube.

FIG. 2A is a simplified cross-section taken on line 2A-2A in FIG. 2. In FIG. 2A, the portion of the catheter system 200 includes an inflation tube 219 and one or more energy guides 222A (only one energy guide 222A is labeled in FIG. 2A). In certain embodiments, the energy guides 222A can be coupled to the guidewire lumen 218 and/or the inflation tube 219, or the energy guides 222A and/or the inflation tube 219 can be positioned in grooves or channels (not shown) in the guidewire lumen 218. As provided in greater detail herein, the inflation tube 219 can be fully open, at least partially collapsed and/or fully collapsed along at least a portion of one of the first tube length 218X (illustrated in FIG. 2) and/or at least a portion of the second tube length 218Y (illustrated in FIG. 2). In other embodiments, the inflation tube 219 can be at least partially collapsed and/or fully collapsed along any suitable portion, such as the portion of the inflation tube 219 that is located inside the balloon 204 (e.g., the second tube length 218Y).

The inflation tube 219 can vary depending on the design requirements of the catheter system 200, the balloon 204, the catheter shaft 210, the guidewire 212, the guidewire lumen 218, and/or the energy guides 222A. It is understood that the inflation tube 219 can include additional components, systems, subsystems, and elements other than those specifically shown and/or described herein. Additionally, or alternatively, the inflation tube 219 can omit one or more of the components, systems, subsystems, and elements that are specifically shown and/or described herein. In some embodiments, various components of the inflation tube 219 can be positioned differently than what is specifically illustrated in the figures.

In various embodiments, the inflation tube 219 can be at least partially formed from a synthetic material, a natural material, a plastic, a polymer, a thermal material, and/or a composite material. Suitable polymers can include Pebax, Urethane, and/or Nylon, or any other suitable polymer. In various embodiments, the inflation tube 219 can be formed to have a reduced form factor in a collapsed configuration (e.g., as shown in FIGS. 3B-3C, for example, also sometimes referred to herein as a "second configuration"). The inflation tube 219 can include materials and/or elements that preferentially cause the inflation tube 219 to be biased toward the collapsed configuration (e.g., at rest, not under pressure). The inflation tube 219 can be formed so that only portions of the inflation tube 219 are thermally formed. The inflation tube 219 can also include one or more thermal bonds (not shown) that fuse extrusions of varying polymers. In certain embodiments, using the thermal bonds to bias the inflation tube 219 into either the collapsed configuration (as illustrated in FIGS. 3B-3C) or the open configuration (illustrated in FIG. 3A).

Figure 3A:
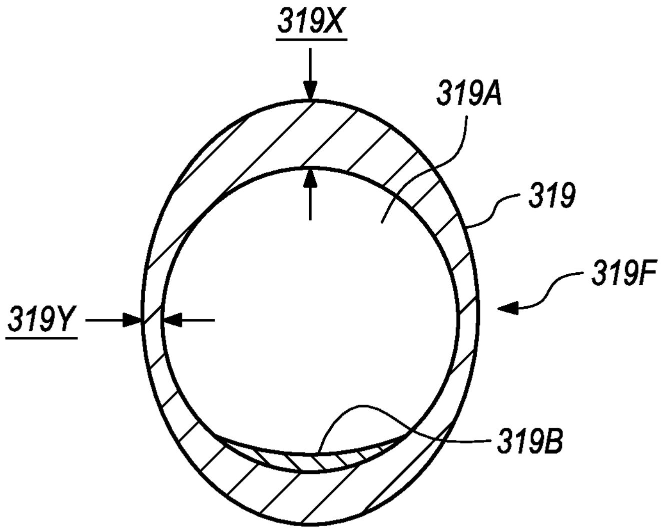
FIG. 3A is a cross-sectional view of one embodiment of the inflation tube illustrated in an open configuration.
Figure 3B:
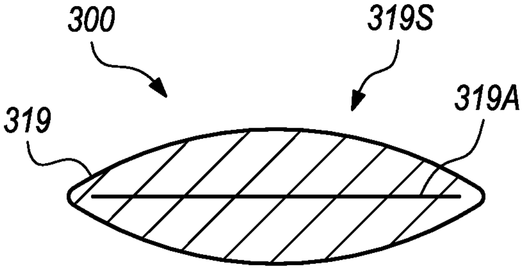
FIG. 3B is a cross-sectional view of the inflation tube illustrated in FIG. 3A, illustrated in a collapsed configuration.
Figure 3C:
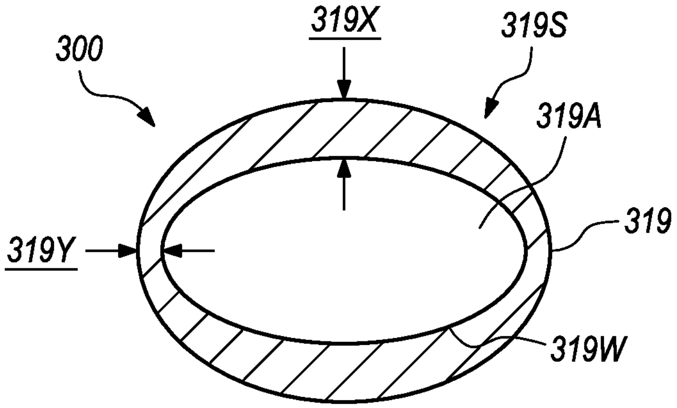
FIG. 3C is a cross-sectional view of the inflation tube illustrated in FIG. 3A, illustrated in another embodiment of the collapsed configuration.

As illustrated in FIGS. 3A-3C, the inflation tube 319 can be movable between (i) a first configuration 319F (also sometimes referred to herein as "the open configuration" illustrated in FIG. 3A) wherein the inflation lumen 319A is essentially fully open, and (ii) a second configuration 319S (also sometimes referred to herein as "a collapsed configuration" illustrated in FIGS. 3B-3C) wherein the inflation lumen 319A is at least partially collapsed relative to the first configuration 319F. Stated another way, and as illustrated in FIGS. 3A-3C, in the first configuration 319F, the inflation lumen 319A has a cross-sectional area that is greater than a cross-sectional area of the inflation lumen 319A when the inflation tube 319 is in the second configuration 319S.

FIG. 3A is a simplified front view of the inflation tube 319 being shown in the first configuration 319F. In various embodiments, the inflation tube 319 can have a first tube wall thickness 319X and a second wall thickness 319Y. In some embodiments, the first wall thickness 319X can have a greater thickness than the second tube wall thickness 319Y. In certain embodiments, the inflation tube 319 has varying wall thicknesses 319X, 319Y. The use of the "first" and "second" tube wall thicknesses are used to show relative thicknesses for clarity. It is understood that the inflation tube 319 can include any suitable number of tube wall 319W thicknesses or an infinite number of thicknesses of the tube wall 319W. The first configuration 319F of the inflation tube 319 has a somewhat larger profile than the second configuration 319S of the inflation tube 319. In the first configuration 319F, in certain embodiments such as that illustrated in FIG. 3A, the inflation lumen 319A can have a substantially circular cross-sectional shape. Alternatively, in the first configuration 319F, the inflation lumen 319A can have a somewhat different cross-sectional shape. In various embodiments (illustrated in FIGS. 3B-3C), it is advantageous to have a somewhat smaller profile of the inflation tube 319, for example during insertion or removal of the catheter 100, or anytime prior to or after inflation of the balloon 104 (illustrated in FIG. 1), or at other suitable times.

In certain embodiments, the inflation tube 319 can include a tube adhesive 319B that is configured to enable the inflation tube 319 and/or the tube wall 319W to adhere to itself. The tube adhesive 319B can vary depending on the design requirements of the inflation tube 319 and/or the tube wall 319W, but can include any suitable adhesive material that can adhere one portion of the inflation tube 319 to another portion of the inflation tube 319. The tube adhesive 319B is simplified in FIG. 3B for ease of understanding and clarity. It is appreciated that the tube adhesive 319B can be applied to any suitable portion of the inflatable tube 319. In various embodiments, the tube adhesive 319B may be a coating or layer coupled to the tube wall 319W. In some embodiments, the inflation tube 319 can impose a bias force on itself so that it is biased toward the second configuration 319S.

In some embodiments, the adherence of the inflation tube 319 relative to itself can be overcome when pressure inside the inflation tube 319 reaches a predetermined threshold level. In one non-exclusive embodiment, a fluid pressure of the inflation fluid 132 (illustrated in FIG. 1) that moves through the inflation tube 319 can cause the inflation tube 319 to move to the first configuration 319F and/or remain in the first configuration 319F for a period of time. This threshold level of pressurization can overcome the adherence of the tube adhesive 319B and can allow the inflation tube 319 to move to the first configuration 319F, creating a larger cross-sectional area of the inflation lumen 319A for the inflation fluid 132 (illustrated in FIG. 1) to move through the inflation tube 319. The threshold level of pressurization can vary depending on the design requirements of the inflation tube 319 and/or the tube adhesive 319B (for example, as illustrated in FIG. 3A).

The inflation tube 319 can also be movable between the first configuration 319F and second configuration 319S by other external and/or internal forces. In other embodiments, the inflation tube 319 can be configured so that the inflation lumen 319A at least partially collapses and/or at least partially expands. As non-limiting, non-exclusive examples, external forces that can be used to move the inflation tube 319 between the first configuration 319F and the second configuration 319S can include pressure forces, thermal forces, and/or electrically-induced forces.

In certain embodiments, as non-limiting, non-exclusive examples, internal forces that can be used to move the inflation tube 319 between the first configuration 319F and the second configuration 319S can include pressure forces, thermal forces, and/or electrically-induced forces. In some embodiments, the inflation tube 319 can be moved to the first configuration 319F using one of an inflator (e.g., an inflation hub 458, illustrated in FIG. 4) and/or a pump (e.g., a fluid pump 438, illustrated in FIG. 4). In other embodiments, the inflation tube 319 can be internally pressurized into the first configuration 319F. Upon removal of at least a portion of the pressurization, the inherent bias of the inflation tube 319 can move the inflation tube 319 to the second configuration 319S.

FIG. 3B is a simplified cross-sectional view of an embodiment of a portion of the catheter system 300, with the inflation tube 319 shown in the second configuration 319S. In the second configuration illustrated in FIG. 3B, the inflation lumen 319A of the inflation tube 319 is essentially fully collapsed such that a cross-sectional area of the inflation lumen 319A is approximately zero. In the embodiment illustrated in FIG. 3B, the inflation tube 319 has a first tube wall thickness 319X, and a second tube wall thickness 319Y that is different than the first tube wall thickness 319X to facilitate movement between the first configuration 319F and the second configuration 319S.

FIG. 3C is a simplified cross-sectional view of an embodiment of a portion of the catheter system 300, with the inflation tube 319 shown in the second configuration 319S wherein the inflation tube 319 is not fully collapsed, but is only partially collapsed relative to the first configuration 319F. In this embodiment, the inflation tube 319 can have a first tube wall thickness 319X and a second tube wall thickness 319Y that is different than the first tube wall thickness 319X to facilitate movement between the first configuration 319F and the second configuration 319S. In the embodiment illustrated in FIG. 3C, a second cross-sectional area of the inflation lumen 319A is reduced from that of the first cross-sectional area of the first configuration 319F, but is greater than that of the inflation lumen 319A illustrated in FIG. 3B. For example, in the embodiment illustrated in FIG. 3C, the second cross-sectional area can have a somewhat elliptical cross-sectional shape, or another modified cross-sectional shape that is different than a circular shape. In an alternative embodiment, the first wall thickness 319X can be the same or substantially similar to the second wall thickness 319Y.

In various non-exclusive alternative embodiments, the second cross-sectional area can be less than: 90%, 75%, 50%, 40%, 30%, 25%, 20%, 15%, 10% or 5% of the first cross-sectional area.

Figure 4:
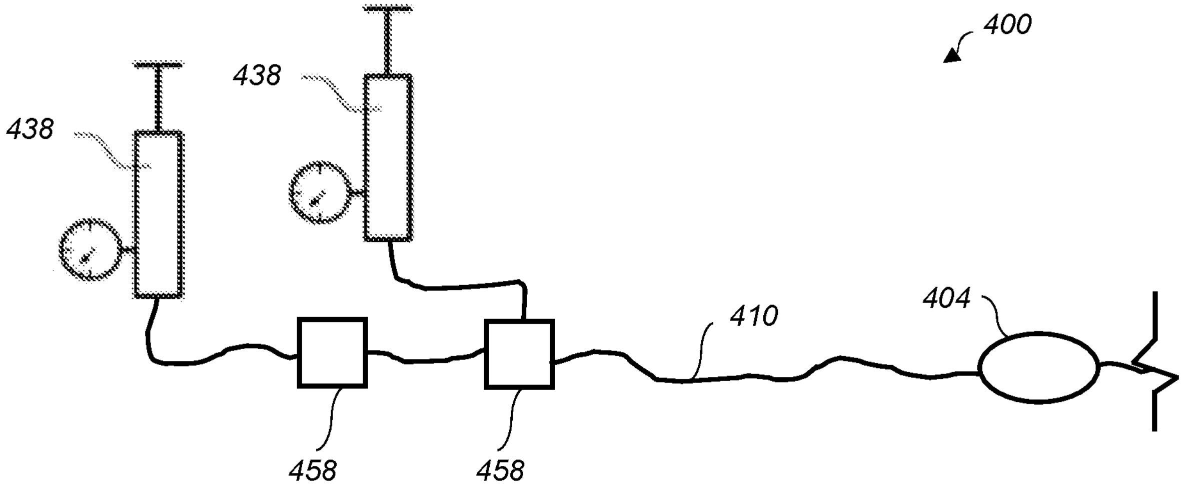
FIG. 4 is a simplified schematic diagram of yet another embodiment of a portion of the catheter system.

FIG. 4 is a simplified schematic diagram of yet another embodiment of a portion of the catheter system 400. In FIG. 4, the catheter system 400 can include a balloon 404, a catheter shaft 410, a fluid pump 438, and/or an inflation hub 458.

The inflation hub 458 can control the inflation of the balloon 404, a guidewire lumen 218 (illustrated in FIG. 2), and/or an inflation tube 319 (illustrated in FIG. 3). In some embodiments, one fluid pump 438 and one inflation hub 458 can work in cooperation to inflate/deflate the inflation tube 319, and one fluid pump 438 and one inflation hub 458 can work in cooperation to inflate/deflate the guidewire lumen 218.

The inflation hub 458 can vary depending on the design requirements of the catheter system 400, the balloon 404, the catheter shaft 410, the guidewire lumen 218, the inflation tube 319, and/or the fluid pump 438. It is understood that the inflation hub 458 can include additional components, systems, subsystems, and elements other than those specifically shown and/or described herein. Additionally, or alternatively, the inflation hub 458 can omit one or more of the components, systems, subsystems, and elements that are specifically shown and/or described herein. In some embodiments, various components of the inflation hub 458 can be positioned differently than what is specifically illustrated in the figures.

While two fluid pumps 438 and two inflation hubs 458 are illustrated in FIG. 4, it is appreciated that the catheter system 400 can include less than two fluid pumps 438 and two inflation hubs 458 or greater than two fluid pumps 438 and two inflation hubs 458.

Figure 5:
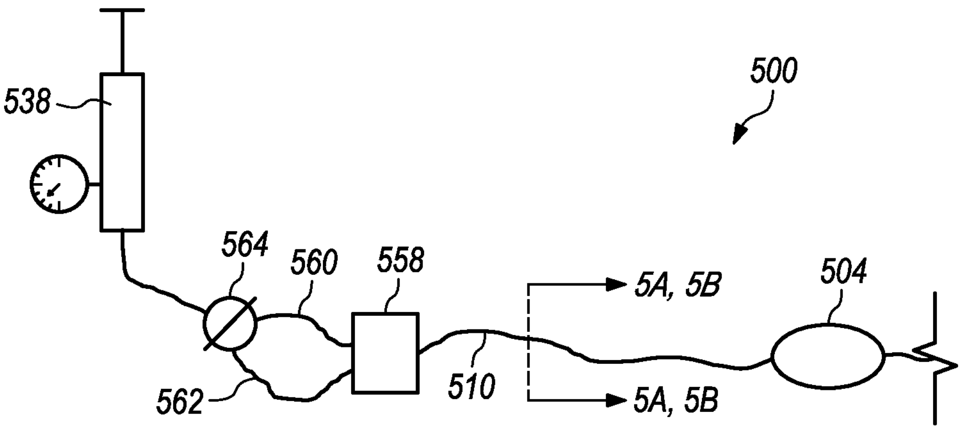
FIG. 5 is a simplified schematic diagram of yet another embodiment of a portion of the catheter system.

FIG. 5 is a simplified schematic diagram of yet another embodiment of a portion of the catheter system 500. In FIG. 5, the catheter system 500 includes a balloon 504, a catheter shaft 510, a fluid pump 538, an inflation hub 558, a first inflation guide 560, a second inflation guide 562, and an inflation director 564.

The first inflation guide 560 can receive inflation from the fluid pump 538 and guide the inflation fluid 132 (illustrated in FIG. 1) via the inflation tube 519 (illustrated in FIGS. 5A-5B, for example) toward the balloon 504. In other embodiments, the first inflation guide 560 can receive fluid from the fluid pump 538 and guide the inflation fluid 132 toward a guidewire lumen 518 (illustrated in FIGS. 5A-5B).

The second inflation guide 562 can receive inflation from the fluid pump 538 and guide the inflation toward the guidewire lumen 518 and/or the inflation hub 558. In other embodiments, the first inflation guide 560 can receive fluid from the fluid pump 538 and guide the fluid via the inflation tube 519. The first inflation guide 560 and the second inflation guide 562 can vary depending on their design requirements and/or the design requirements of the catheter system 500.

The inflation director 564 can direct inflation from the fluid pump 538 toward the first inflation guide 560 and/or the second inflation guide 562. The inflation director 564 can control the flow of liquids, gases, and/or inflation through the catheter system 500. The inflation director 564 can also be configured to reduce and/or prevent the flow of liquids, gases, and/or inflation through the catheter system 500. The inflation director 564 can vary depending on its design requirements and/or the design requirements of the catheter system 500. The inflation director 564 can include a directional valve and/or a three-way stopcock valve.

Figure 5A:
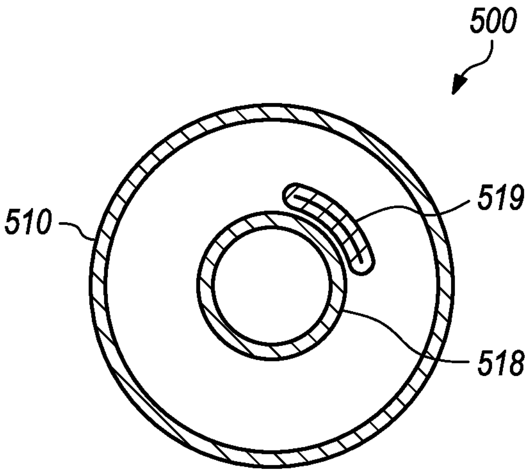
FIG. 5A is a simplified cross-sectional illustration taken on line 5A-5A in FIG. 5, showing the inflation tube in a collapsed configuration.

FIG. 5A is a simplified cross-section taken on line 5A-5A in FIG. 5. In this embodiment, the inflation tube 519 is shown in the second (fully collapsed) configuration 319S (illustrated in FIG. 3B).

Figure 5B:
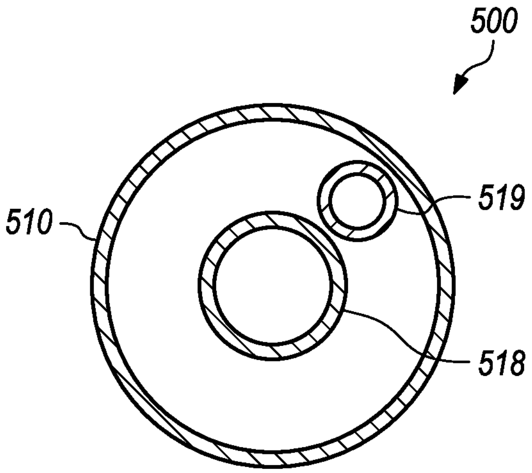
FIG. 5B is a simplified cross-sectional illustration taken on line 5B-5B in FIG. 5, showing the inflation tube in an open configuration.

FIG. 5B is a simplified cross-section taken on line 5B-5B in FIG. 5. In this embodiment, the inflation tube 519 is shown in the second (reduced) configuration 319S (illustrated in FIG. 3B), but not fully collapsed.

Figure 6:
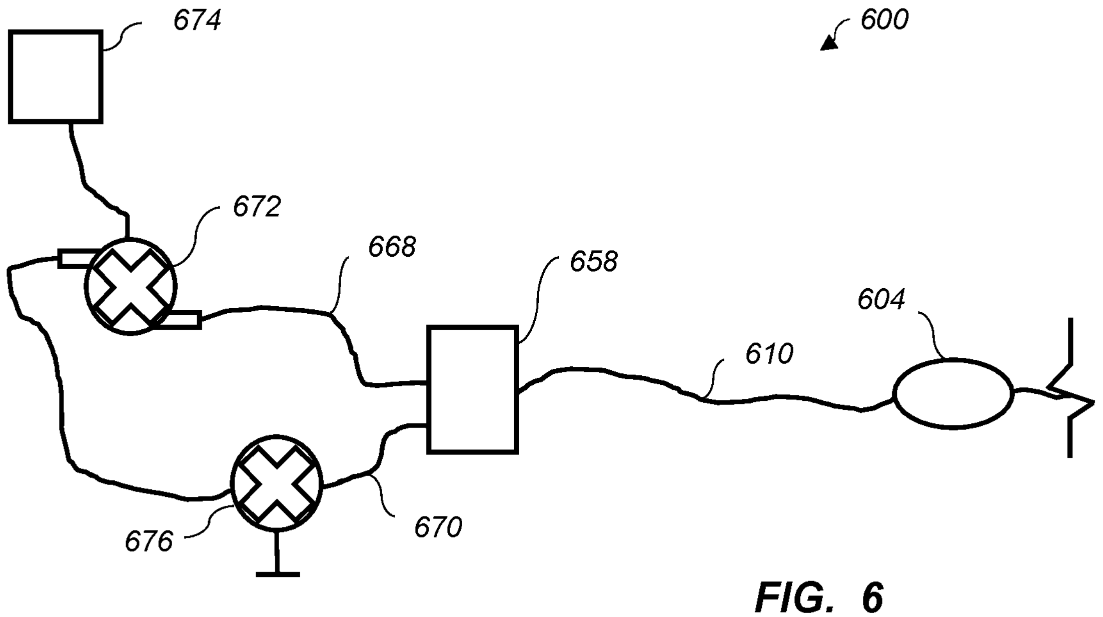
FIG. 6 is a simplified schematic diagram of yet another embodiment of a portion of the catheter system.

FIG. 6 is a simplified schematic diagram of yet another embodiment of a portion of the catheter system 600. In FIG. 6, the catheter system 600 includes a balloon 604, a catheter shaft 610, an inflation hub 658, an inflow 668, an outflow 670, a circulatory pump 672, a reservoir 674, and/or a check valve 676.

The inflow 668 can guide the flow of inflation, fluids, and/or gases from the circulatory pump 672 to the inflation hub 658. The inflation hub 658 can control the inflation and/or deflation of the guidewire lumen 518 (illustrated in FIG. 5) and/or the inflation tube 519 (illustrated in FIG. 5).

Following deflation, the outflow 670 can guide the flow of inflation, fluids, and/or gases toward the check valve 676 in one direction (e.g., in the closed loop pump illustrated in FIG. 6, in the clockwise direction). The reservoir 674 can hold the gases and/or liquids used to operate the catheter system 600 inflation and deflation.

The present invention is also directed toward methods for treating a treatment site within or adjacent to a vessel wall or heart valve, with such methods utilizing the devices disclosed herein.

Lasers

The lasers suitable for use herein can include various types of lasers, including lasers and lamps. Suitable lasers can include short pulse lasers on the sub-millisecond timescale. In some embodiments, the laser can include lasers on the nanosecond (ns) timescale. The lasers can also include short pulse lasers on the picosecond (ps), femtosecond (fs), and microsecond (us) timescales. It is appreciated that there are many combinations of laser wavelengths, pulse widths, and energy levels that can be employed to achieve plasma in the inflation fluid of the catheters illustrated and/or described herein. In various embodiments, the pulse widths can include those falling within a range including from at least 10 ns to 200 ns. In some embodiments, the pulse widths can include those falling within a range including from at least 20 ns to 100 ns. In other embodiments, the pulse widths can include those falling within a range including from at least 1 ns to 5000 ns.

Exemplary nanosecond lasers can include those within the UV to IR spectrum, spanning wavelengths of about 10 nanometers to 1 millimeter. In some embodiments, the lasers suitable for use in the catheter systems herein can include those capable of producing light at wavelengths of from at least 750 nm to 2000 nm. In some embodiments, the lasers can include those capable of producing light at wavelengths of from at least 700 nm to 3000 nm. In some embodiments, the lasers can include those capable of producing light at wavelengths of from at least 100 nm to 10 micrometers (μm). Nanosecond lasers can include those having repetition rates of up to 200 kHz. In some embodiments, the laser can include a Q-switched thulium:yttrium-aluminum-garnet (Tm:YAG) laser. In some embodiments, the laser can include a neodymium:yttrium-aluminum-garnet (Nd:YAG), holmium:yttrium-aluminum-garnet (Ho:YAG), erbium:yttrium-aluminum-garnet (Er:YAG), excimer laser, helium-neon laser, carbon dioxide laser, as well as doped, pulsed, fiber lasers.

Pressure Waves

The catheters illustrated and/or described herein can generate pressure waves having maximum pressures in the range of at least 1 megapascal (MPa) to 100 MPa. The maximum pressure generated by a particular catheter will depend on the laser, the absorbing material, the bubble expansion, the propagation medium, the balloon material, and other factors. In some embodiments, the catheters illustrated and/or described herein can generate pressure waves having maximum pressures in the range of at least 2 MPa to 50 MPa. In other embodiments, the catheters illustrated and/or described herein can generate pressure waves having maximum pressures in the range of at least 2 MPa to 30 MPa. In yet other embodiments, the catheters illustrated and/or described herein can generate pressure waves having maximum pressures in the range of at least 15 MPa to 25 MPa. In some embodiments, the catheters illustrated and/or described herein can generate pressure waves having peak pressures of greater than or equal to 1 MPa, 2 MPa, 3 MPa, 4 MPa, 5 MPa, 6 MPa, 7 MPa, 8 MPa, 9 MPa, 10 MPa, 11 MPa, 12 MPa, 13 MPa, 14 MPa, 15 MPa, 16 MPa, 17 MPa, 18 MPa, 19 MPa, 20 MPa, 21 MPa, 22 MPa, 23 MPa, 24 MPa, or 25 MPa, 26 MPa, 27 MPa, 28 MPa, 29 MPa, 30 MPa, 31 MPa, 32 MPa, 33 MPa, 34 MPa, 35 MPa, 36 MPa, 37 MPa, 38 MPa, 39 MPa, 40 MPa, 41 MPa, 42 MPa, 43 MPa, 44 MPa, 45 MPa, 46 MPa, 47 MPa, 48 MPa, 49 MPa, or 50 MPa. It is appreciated that the catheters illustrated and/or described herein can generate pressure waves having operating pressures or maximum pressures that can fall within a range, wherein any of the foregoing numbers can serve as the lower or upper bound of the range, provided that the lower bound of the range is a value less than the upper bound of the range.

Therapeutic treatment can act via a fatigue mechanism or a brute force mechanism. Pressures between the extreme ends of these two ranges may act upon a treatment site using a combination of a fatigue mechanism and a brute force mechanism. For a fatigue mechanism, operating pressures would be about at least 0.5 MPa to 2 MPa, or about 1 MPa. For a brute force mechanism, operating pressures would be about at least 20 MPa to 30 MPa, or about 25 MPa.

The pressure waves described herein can be imparted upon the treatment site from a distance within a range from at least 0.01 millimeters (mm) to 25 mm, extending radially from a longitudinal axis of a catheter placed at a treatment site. In some embodiments, the pressure waves can be imparted upon the treatment site from a distance within a range from at least 1 mm to 20 mm, extending radially from a longitudinal axis of a catheter placed at a treatment site. In other embodiments, the pressure waves can be imparted upon the treatment site from a distance within a range from at least 0.1 mm to 10 mm, extending radially from a longitudinal axis of a catheter placed at a treatment site. In yet other embodiments, the pressure waves can be imparted upon the treatment site from a distance within a range from at least 1.5 mm to 4 mm, extending radially from a longitudinal axis of a catheter placed at a treatment site. In some embodiments, the pressure waves can be imparted upon the treatment site from a range of at least 2 MPa to 30 MPa at a distance from 0.1 mm to 10 mm. In some embodiments, the pressure waves can be imparted upon the treatment site from a range of at least 2 MPa to 25 MPa at a distance from 0.1 mm to 10 mm. In some embodiments, the pressure waves can be imparted upon the treatment site from a distance that can be greater than or equal to 0.1 mm, 0.2 mm, 0.3 mm, 0.4 mm, 0.5 mm, 0.6 mm, 0.7 mm, 0.8 mm, or 0.9 mm, 1 mm, 2 mm, 3 mm, 4 mm, 5 mm, 6 mm, 7 mm, 8 mm, 9 mm, or 10 mm, or can be an amount falling within a range between, or outside the range of any of the foregoing.

By shaping the temporal form of the optical pulse to have a fast rise time and minimal overshoot (in some embodiments, approaching a square wave), the efficiency for generating the pressure wave can be improved, and the amount of energy that can be delivered in a given time interval can be increased while decreasing the peak laser intensity to remain below the damage threshold of the optical fiber.

It should be noted that, as used in this specification and the appended claims, the singular forms "a," "an," and "the" include plural referents unless the content and/or context clearly dictates otherwise. It should also be noted that the term "or" is generally employed in its sense, including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

As used herein, the recitation of numerical ranges by endpoints shall include all numbers subsumed within that range, inclusive (e.g., 2 to 8 includes 2, 2.1, 2.8, 5.3, 7, 8, etc.).

It is recognized that the figures shown and described are not necessarily drawn to scale, and that they are provided for ease of reference and understanding, and for relative positioning of the structures.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter systems have been illustrated and described herein, one or more features of any one embodiment can be combined with one or more features of one or more of the other embodiments, provided that such combination satisfies the intent of the present invention.

While a number of exemplary aspects and embodiments of the catheter systems have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope, and no limitations are intended to the details of construction or design herein shown.

What is claimed is:

1. A catheter system for treating a treatment site within or adjacent to a vessel wall or a heart valve, the catheter system comprising:

a balloon having a balloon interior;

an outer shaft having an inner surface defining an outer shaft lumen and a distal end coupled to the balloon;

an inner shaft having an outer surface and extending within at least a portion of the lumen of the outer shaft and the balloon interior, and having an inner surface defining an inner shaft lumen to receive a guidewire; and an inflation tube positioned between the outer surface of the inner shaft and the inner surface of the outer shaft, wherein the inflation tube is configured to guide a flow of an inflation fluid into the balloon interior, the inflation tube having an inflation lumen, the inflation tube being movable between (i) an first configuration wherein the inflation lumen has a first cross-sectional area, and (ii) a second configuration wherein the inflation lumen has a second cross-sectional area that is less than the first cross-sectional area, the inflation tube being at least partially formed from a first polymer and a second polymer that is different than the first polymer, the first polymer and the second polymer being thermally bonded to one another.

2. The catheter system of claim 1 wherein the inflation tube is biased toward the second configuration.

3. The catheter system of claim 2 wherein the inflation tube is configured to be moved to the first configuration using fluid pressure.

4. The catheter system of claim 1 wherein the inflation tube is biased toward the first configuration.

5. The catheter system of claim 1 wherein the inflation tube is at least partially formed from one of a plastic, a synthetic material and a natural material.

6. The catheter system of claim 1 wherein the inflation tube includes a tube wall that varies in thickness.

7. The catheter system of claim 1 wherein the inflation tube is fully collapsible so that the second cross-sectional area of the inflation lumen is approximately equal to zero.

8. The catheter system of claim 1 wherein in the second configuration a cross-sectional shape of the inflation tube is substantially elliptical.

9. The catheter system of claim 1 wherein in the first configuration a cross-sectional shape of the inflation tube is substantially circular.

10. The catheter system of claim 1 wherein the inflation tube includes a tube adhesive so that the inflation tube is adherable to itself when the inflation tube is in the second configuration.

11. The catheter system of claim 1 wherein the inflation tube has a tube length, and the inflation tube is configured to move to the second configuration along at least a portion of the tube length.

12. The catheter system of claim 1 wherein the inflation tube has a tube length, and the inflation tube is thermally formed along at least a portion of the tube length.

13. A catheter system for treating a treatment site within or adjacent to a vessel wall or a heart valve, the catheter system comprising:

a balloon having a balloon interior;

an outer shaft having an inner surface defining an outer shaft lumen and a distal end coupled to the balloon;

an inner shaft having an outer surface directly coupled to the balloon and extending within at least a portion of the lumen of the outer shaft and the balloon interior; and an inflation tube positioned between the outer surface of the inner shaft and the inner surface of the outer shaft, wherein the inflation tube is configured to guide a flow of an inflation fluid into the balloon interior, the inflation tube having an inflation lumen, the inflation tube being movable between (i) an first configuration wherein the inflation lumen has a first cross-sectional area, and (ii) a second configuration wherein the inflation lumen has a second cross-sectional area that is less than the first cross-sectional area, the inflation tube including one or more thermal bonds that are configured to fuse extrusions of varying polymers that at least partially form the inflation tube.

14. The catheter system of claim 13 wherein the inflation tube is biased toward the second configuration.

15. The catheter system of claim 14 wherein the inflation tube is configured to be moved to the first configuration using fluid pressure.

16. The catheter system of claim 13 wherein the inflation tube is biased toward the first configuration.

17. The catheter system of claim 13 wherein the inflation tube is at least partially formed from one of a plastic, a synthetic material and a natural material.

18. The catheter system of claim 13 wherein the inflation tube includes a tube wall that varies in thickness.

19. The catheter system of claim 13 wherein the inflation tube is fully collapsible so that the second cross-sectional area of the inflation lumen is approximately equal to zero.

20. A catheter system for treating a treatment site within or adjacent to a vessel wall or a heart valve, the catheter system comprising:

a balloon having a balloon interior;

an outer shaft having an inner surface defining an outer shaft lumen and a distal end coupled to the balloon;

an inner shaft having an outer surface, having an inner surface defining an inner shaft lumen to receive a guidewire, and extending within at least a portion of the lumen of the outer shaft and the balloon interior; and an inflation tube positioned between the outer surface of the inner shaft and the inner surface of the outer shaft, wherein the inflation tube is configured to guide a flow of an inflation fluid into the balloon interior, the inflation tube having an inflation lumen, the inflation tube being movable between (i) an first configuration wherein the inflation lumen has a first cross-sectional area, and (ii) a second configuration wherein the inflation lumen has a second cross-sectional area that is less than the first cross-sectional area, the inflation tube being at least partially formed from a first polymer and a second polymer that is different than the first polymer, the first polymer and the second polymer being thermally bonded to one another, the inflation tube including one or more thermal bonds that are configured to fuse extrusions of varying polymers that at least partially form the inflation tube.

* * * * *